United States Patent
Bathe et al.

(10) Patent No.: US 10,289,799 B2
(45) Date of Patent: May 14, 2019

(54) TECHNIQUES FOR CONTROLLING SPATIAL STRUCTURE OF NUCLEIC ACID STRUCTURES BASED ON LATTICE-FREE, THREE DIMENSIONAL JUNCTION COORDINATES

(71) Applicants: Mark Bathe, Cambridge, MA (US); Keyao Pan, Cambridge, MA (US); Do-Nyun Kim, Seoul (KR)

(72) Inventors: Mark Bathe, Cambridge, MA (US); Keyao Pan, Cambridge, MA (US); Do-Nyun Kim, Seoul (KR)

(73) Assignee: Massachusetts Institute of Technology, Cambridge, MA (US)

( * ) Notice: Subject to any disclaimer, the term of this patent is extended or adjusted under 35 U.S.C. 154(b) by 490 days.

(21) Appl. No.: 14/874,417

(22) Filed: Oct. 3, 2015

(65) Prior Publication Data

US 2016/0103951 A1    Apr. 14, 2016

Related U.S. Application Data

(60) Provisional application No. 62/059,795, filed on Oct. 3, 2014.

(51) Int. Cl.
| | | |
|---|---|---|
| *G01N 33/48* | (2006.01) | |
| *G06F 15/00* | (2006.01) | |
| *G06F 19/16* | (2011.01) | |
| *G06F 19/26* | (2011.01) | |

(52) U.S. Cl.
CPC ............. *G06F 19/16* (2013.01); *G06F 19/26* (2013.01)

(58) Field of Classification Search
None
See application file for complete search history.

(56) References Cited

U.S. PATENT DOCUMENTS

2012/0166152 A1    6/2012    Bathe et al.

OTHER PUBLICATIONS

Bernstein, F. C., et al., "The Protein Data Bank a Computer-Based Archival File for Macromolecular Structures," Eur. J. Biochem, 1977, pp. 319-324, vol. 80.

Castro, C. E., et al., "A primer to scaffolded DNA origami;" Nature Methods, 2011, pp. 221-229 and Supplemental pp. 1-30, vol. 8, No. 3, Publisher: Nature America, Inc., DOI: 10.1038/nmeth.1570.

Douglas, S. M., et al., "Rapid prototyping of 3D DNA-origami shapes with caDNAno," Nucleic Acids Research, 2009, pp. 5001-5006, vol. 37, No. 15, DOI: 10.1093/nar/gkp436.

Kim, D., et al., "Quantitative prediction of 3D solution shape and flexibility of nucleic acid nanostructures," Nucleic Acids Research, 2012, pp. 2862-2868 and Supplemental pp. 1-27, vol. 40, No. 7, Publisher: Oxford University Press, DOI: 10.1093/nar/gkr1173.

Kim, D., et al., "Biopshysical Modeling of Nucleic Acid Nanostructure Solution Shape and Stability," Biophysical Journal, 2013, p. 28a, vol. 104, Issue 2, Publisher: Elsevier.

Mao, C., et al., "Designed Two Dimensional DNA Holliday Junction Arrays Visualized by Atomic Force Microscopy," J. Am. Chem Soc., 1999, pp. 5437-5443, vol. 121.

Pan, K., et al., "Lattice-free prediction of three-dimensional structure of programmed DNA assemblies," Nature Communications, 2014, pp. 1-7, Article 5578, Publisher: Macmillan Publishers Limited, DOI:10.1038/ncomms6578.

Pan, K., et al., "Structure-based model for light-harvesting properties of nucleic acid nanostructures," Nucleic Acids Research, 2013, pp. 2159-2170 and Supplemental pp. 1-14, vol. 42, No. 4, DOI: 10.1093/nar/gkt1269.

Pan, K., et al., "Generalized Holiiday Junction Model for Off-Lattice Prediction of DNA Nanostructure Solution Shape," Poster, undated, p. 1.

Seeman, N., "Nucleic Acid Junctions and Lattices," J. Theor. Biol., 1982, pp. 237-247, vol. 99, Publisher: Academic Press Inc. (London) Ltd.

Seeman, N., et al., "Design of Immobile Nucleic Acid Junctions," Biophys. J., 1983, pp. 201-209, vol. 44, Publisher: Biophysical Society.

USPTO, International Search Report and Written Opinion, International Patent Application No. PCT/US2015/053894, dated Dec. 31, 2015, 6 pages.

*Primary Examiner* — Anna Skibinsky
(74) *Attorney, Agent, or Firm* — Eugene J. Molinelli; Beusse Wolter Sanks & Maire

(57) ABSTRACT

Techniques for controlling nucleic acid structures include determining, for each junction type, values for parameters indicating ground-state geometry and both translational and rotational stiffness coefficients. Topological design data indicates a number of bases in each helix connected to corresponding junctions. Initial positions of each base are determined by connecting helices to junctions using the ground-state geometry and arbitrary coordinates not confined to lattice coordinates. Misalignment vectors each indicate a difference in coordinates and orientations between initial positions of a pair of bases that are not adjacent in the initial positions but are adjacent or coincident in the design data. Forces and moments at the junctions to reduce misalignment magnitudes are determined based on the translational and rotational stiffness coefficients at each junction. Position and orientation in 3D coordinates of each base are determined by reducing or eliminating the misalignment magnitudes and balancing forces and moments across the nanostructure.

16 Claims, 27 Drawing Sheets

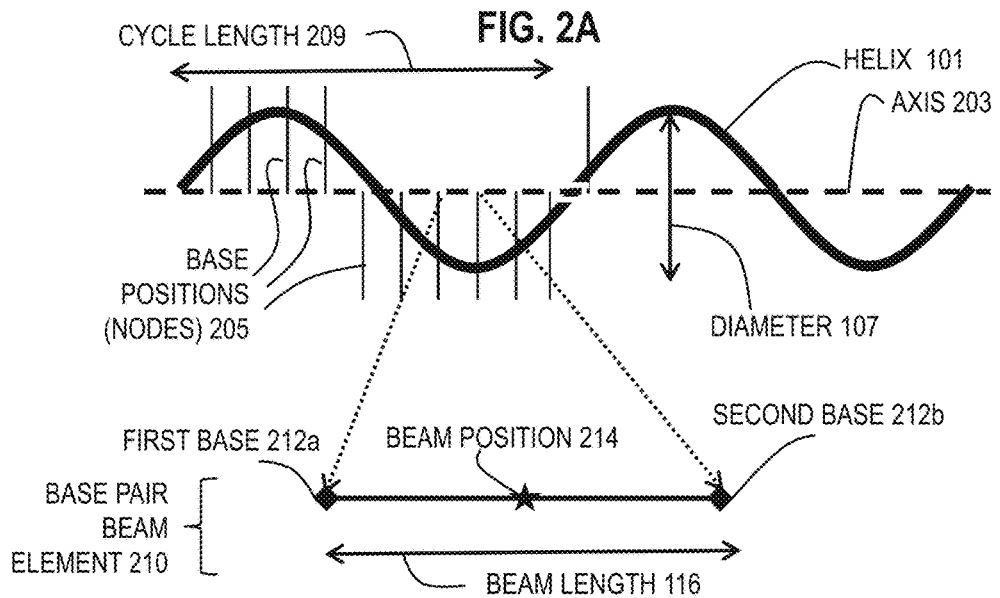
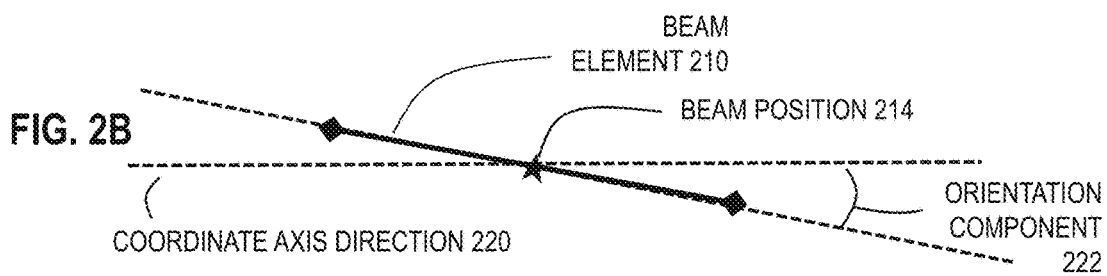

270 Square-Lattice  274 Honeycomb-Lattice

DNA DUPLEX

NICKED DNA DUPLEX

GAPPED DNA DUPLEX ssDNA OVERHANG

ANTIPARALLEL STACKED
4-WAY JUNCTION

OPEN 4-WAY JUNCTION

PARALLEL STACKED
4-WAY JUNCTION

N-WAY JUNCTION

FIG. 4I
| Topological motif | Schematic model | Finite element model |
|---|---|---|
| Duplex 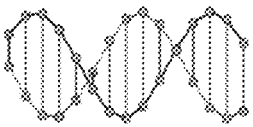 |  | $N$ finite element nodes connected by $N-1$ beam elements 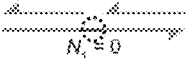 |
| Nick  | 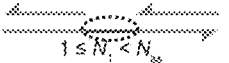 | A beam element  |
| Gap 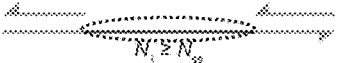 |  | A truss element 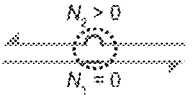 |
| Single-stranded region | | A truss element |
| Bulge | | A beam element |

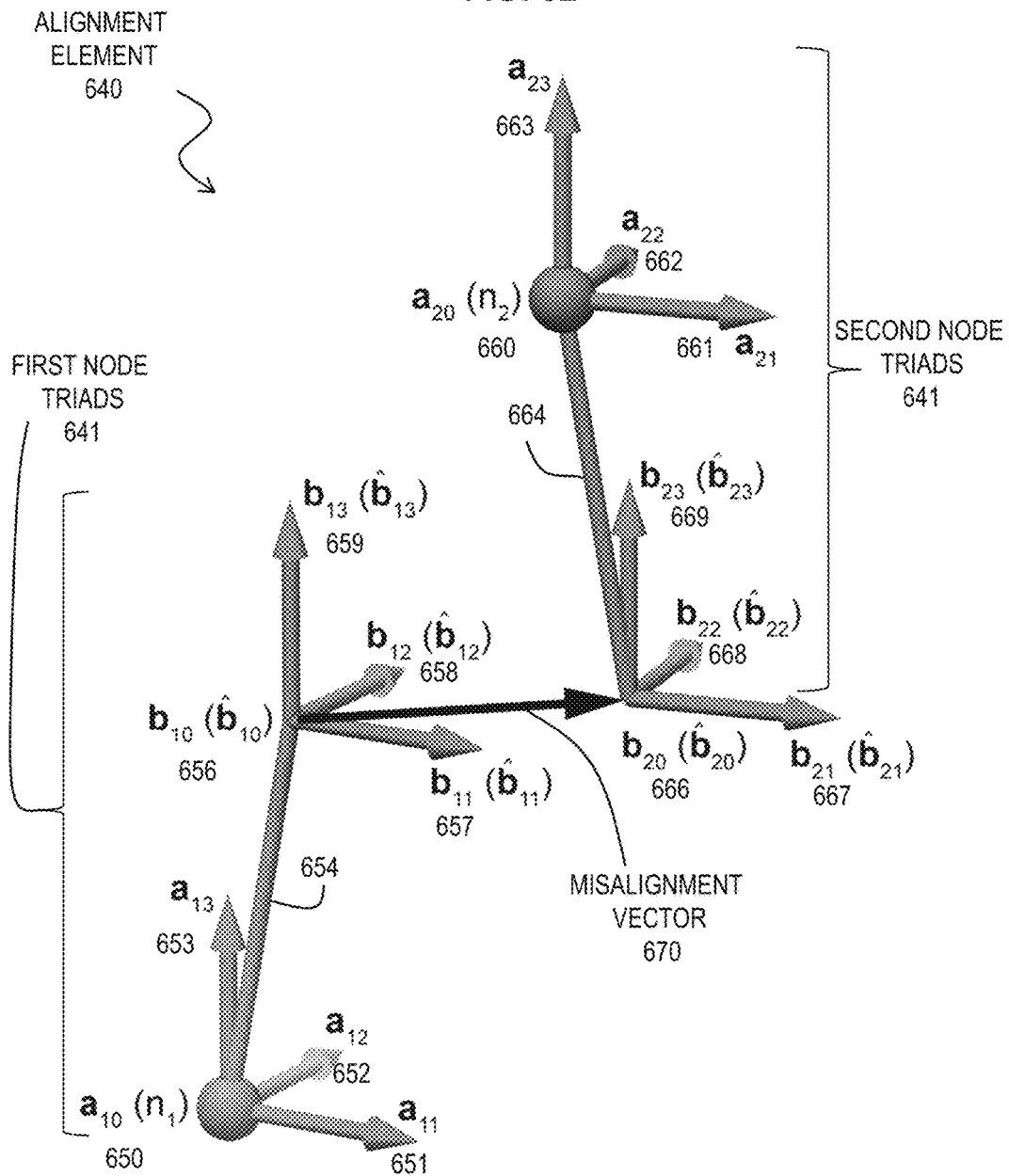

Initial shape

Intermediate shape 1

Intermediate shape 2

Final shape

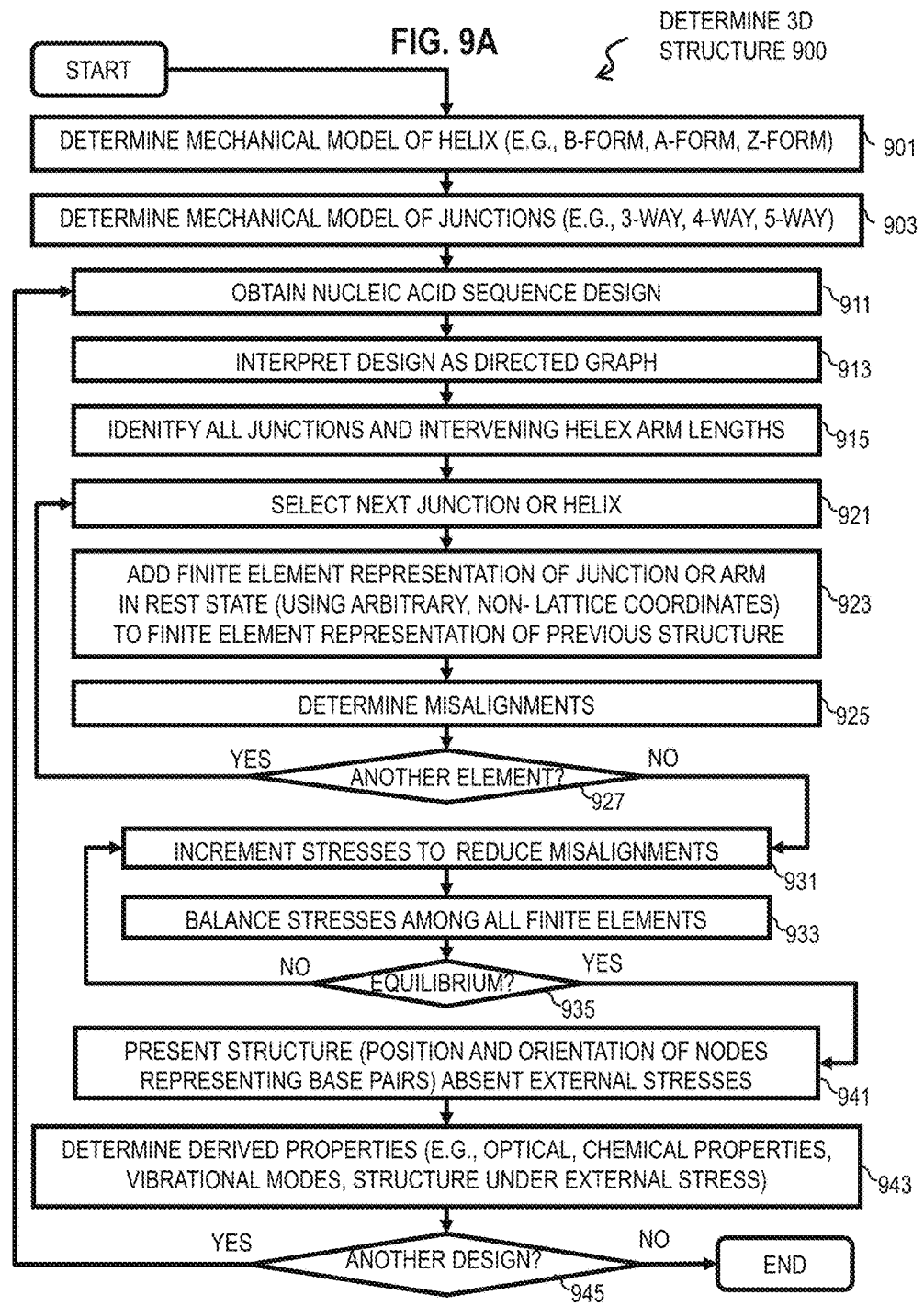

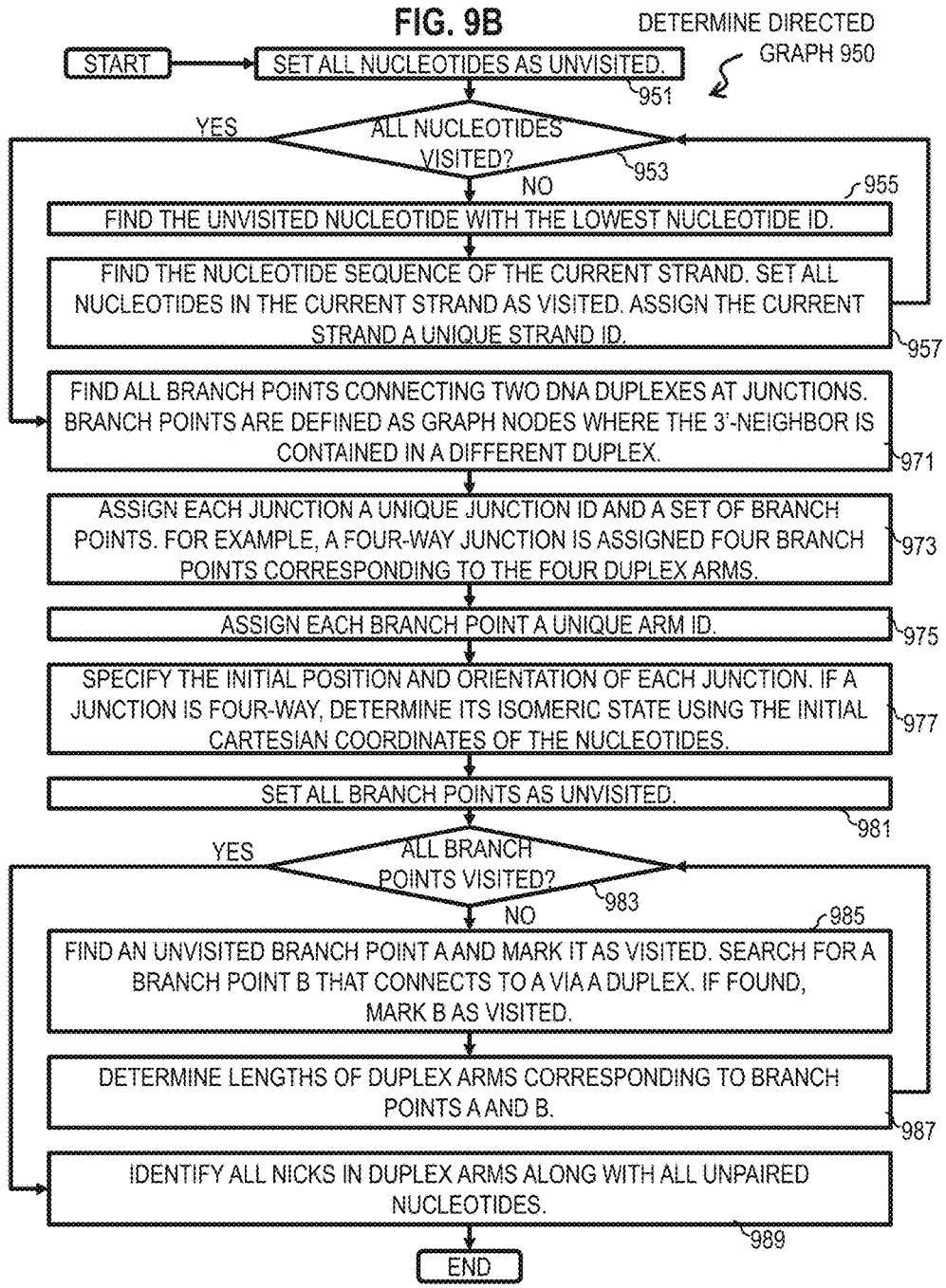

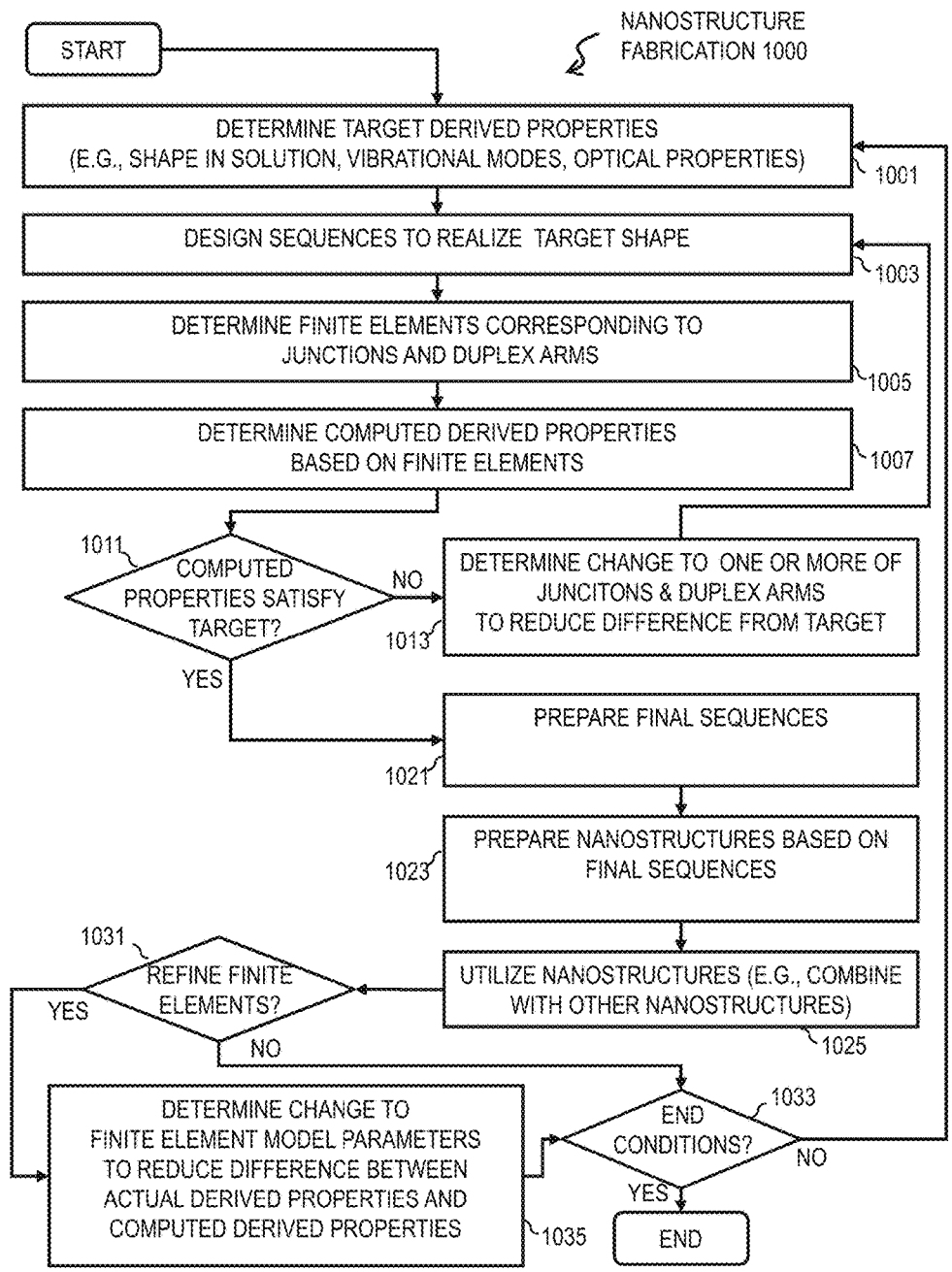

FIG. 11A

| $n_y$ [bp] \ $n_x$ [bp] | 20 (LH) | 21 (F) | 22 (RH) |
|---|---|---|---|
| 20 (RH) | | | |
| 21 (F) | | | |
| 22 (LH) | | | |

FIG. 11B

| $n_y$ [bp] \ $n_x$ [bp] | 20 (LH) | 21 (F) | 22 (RH) |
|---|---|---|---|
| 20 (RH) | LH, RH | F, RH | RH, RH |
| 21 (F) | LH, F | F, F | RH, F |
| 22 (LH) | LH, LH | F, LH | RH, LH |

4-layer ring

TECHNIQUES FOR CONTROLLING SPATIAL STRUCTURE OF NUCLEIC ACID STRUCTURES BASED ON LATTICE-FREE, THREE DIMENSIONAL JUNCTION COORDINATES

CROSS-REFERENCE TO RELATED APPLICATIONS

This application claims benefit of Provisional Appln. 62/059,795, filed 3 Oct. 2014, the entire contents of which are hereby incorporated by reference as if fully set forth herein, under 35 U.S.C. § 119.

STATEMENT OF GOVERNMENTAL INTEREST

This invention was made with government support under Contract No. N000141210621 awarded by the Office of Naval Research. The government has certain rights in the invention.

BACKGROUND

Deoxyribonucleic acid (DNA) can be programmed to self-assemble reliably into diverse megadalton-scale architectures of programmed three dimensional (3D) arrangement (1 megadalton, MDa=$10^6$ daltons, 1 dalton=one twelfth of the mass of an unbound neutral atom of carbon-12 in its nuclear and electronic ground state).

Sequence design principles for programming nucleic acids to self-assemble into highly structured, stable macromolecular assemblies date back to a landmark paper, Seeman, N C. "Nucleic acid junctions and lattices," *Journal of Theoretical Biology* v99, pp237-247, 1982; and, Seeman N C, Kallenbach N R, "Design of immobile nucleic acid junctions," *Biophys J,* v44 (2) pp201-209, 1983 (hereinafter Seeman). In this work, it was illustrated theoretically that canonical Watson-Crick base pairing of complementary DNA strands could in principle be used to program architectures of considerably larger-scale than the double helix itself. The core structural motifs contained in this synthetic macromolecular design paradigm were B-form DNA and the immobile four-way junction (a four-way junction that consists at high magnesium concentration of two antiparallel DNA helices in one of two possible isomeric states).

Since that work, a myriad of two dimensional (2D) and 3D structured nucleic acids have been assembled using the principles established by Seeman, exploiting a variety of topological strategies that include a highly successful approach for synthesizing large-scale DNA assemblies called scaffolded DNA origami. In the origami approach, hundreds of short synthetic single-stranded nucleic acids are combined with a single longer scaffold strand that is typically the M13 phage genome to program megadalton-scale architectures. Examples include brick-like rectilinear and curved assemblies designed on square and honeycomb lattices in which parallel DNA helices are constrained to their topologically adjoined neighbors via stacked four-way junctions, generalized gridiron-like rectilinear and curved objects in 2D and 3D, as well as other examples. In cases where a scaffold strand is not included, single-stranded helices can alternatively be assembled alone to form extended 2D and 3D lattices and crystals.

While rules for pairing nucleic acid bases and assembly conditions to design synthetic DNA architectures are now established, structure-based models that relate underlying DNA topology and base pairing to precise 3D solution structure (position and orientation of bases and base pairs, the latter abbreviated bp) and mechanical properties are lacking. A recent approach used finite element modeling based on coordinates relative to an underlying square or honeycomb (hexagonal) lattice (see D N Kim, F Kilchherr, H Dietz, M Bathe, "Quantitative prediction of 3D solution shape and flexibility of nucleic acid nanostructures," *Nucleic Acids Research,* v40 (7) pp2862-8, 2012; and, K Pan, E Boulais, L Yang, M Bathe, "Structure-based model for light-harvesting properties of nucleic acid nanostructures," *Nucleic Acids Research,* v42 (4), pp 2159-70, 2013, the entire contents of each of which are hereby incorporated by reference as if fully set forth herein). In those approaches, it was assumed that neighboring duplexes are anti-parallel and rigidly constrained to reside on one of several predetermined lattices. While useful, this lattice-based design paradigm is not generally applicable to DNA architectures containing junction motifs that do not reside on one of these lattices, significantly limiting the scope of the paradigm.

SUMMARY

Techniques are provided for reducing the complexity and improving the efficiency and generality of computations of solutions to 3D structure and mechanical properties and optical properties of nucleic acid architectural structures. As used herein, a helix is either a single strand or double strand (duplex) of nucleic acid bases, and refers to a portion of either DNA or ribonucleic acid (RNA) structures.

In a first set of embodiments, a method includes determining, for each junction type of one or more nucleic acid junction types, multiple values corresponding to multiple fixed parameters that indicate a ground-state geometry and translational and rotational junction stiffness coefficients for perturbations from the ground-state geometry. The method also includes obtaining or otherwise determining design data that indicates, for a nucleic acid structure, a number of nucleic acid bases in each helix of a set of two or more helices. The set of helices are joined at a corresponding junction. The design data includes multiple sets of helices in the nucleic acid structure, wherein the plurality of sets of helices are connected by a plurality of junctions. The method also includes determining initial positions of each base in the nucleic acid structure by connecting helices at junctions using the ground-state geometry of each junction, wherein the initial positions are in arbitrary three dimensional coordinates that are not confined to lattice coordinates. The method still further includes determining a set of one or more misalignment vectors. Each misalignment vector indicates a difference in three dimensional coordinates between initial positions of a pair of bases that are not adjacent in the initial positions but are adjacent in the design data. The method yet further includes determining one or more forces or moments or both at the plurality of junctions to reduce magnitudes corresponding to the set of misalignment vectors based on the set of misalignment vectors and the translational and rotational stiffness coefficients at each junction of the plurality of junctions. Even further, the method includes determining a three dimensional structure comprising position and orientation in three dimensional coordinates of each base in the nucleic acid structure, by reducing the magnitudes corresponding to the set of misalignment vectors and balancing forces and moments across the nucleic acid structure.

In some embodiments of the first set, values corresponding to the fixed parameters are constant values.

In some embodiments of the first set, determining one or more forces or moments or both at the multiple junctions includes representing the junctions and helices as elements in a finite element model, and executing the finite element model to incrementally apply forces to incrementally reduce the magnitudes and to propagate the forces through the multiple junctions. In some of these embodiments, the misalignment vectors are represented by alignment elements of the finite element model.

In some embodiments of the first set, the method includes determining, for each helix type of one or more nucleic acid helix types, multiple helix values corresponding to multiple fixed helix parameters that indicate a helix ground-state geometry per base and translational and rotational helix stiffness coefficients for perturbations per base from the helix ground-state geometry per base. In these embodiments, determining initial positions of each base in the nucleic acid structure includes connecting helices at junctions using the helix ground-state geometry of each helix and a number of bases of each helix. In some of these embodiments, determining the one or more forces or moments or both to reduce the magnitudes corresponding to the set of misalignment vectors includes determining one or more forces or moments or both on each helix of the plurality of sets of helices based on the translational and rotational helix stiffness coefficients and a number of bases of each helix. In some of these embodiments, determining the forces at the plurality of junctions includes representing at least one portion of each helix as a beam element in a finite element model and representing each base of the at least one portion as a beam node of the beam element. The finite element model is executed to incrementally apply forces and moments to incrementally reduce the magnitudes and to propagate the forces and moments through the plurality of junctions and plurality of sets of helices.

In some embodiments of the first set, the method includes interpreting the design data as a directed graph to determine each junction in the design data and each helix connected to each junction and a number of bases of each helix.

In some embodiments of the first set, each base in each helix is appended, along with any intervening bases, to one junction to which the helix is connected and all bases in the helix appended to the one junction comprises one arm of the junction.

In some embodiments of the first set, each misalignment vector also indicates a difference in orientation of the pair of bases that are not adjacent in the initial positions but are adjacent in the design data.

In other sets of embodiments, a computer readable-medium, an apparatus and a system are configured to perform one or more steps of the above methods.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 2A to FIG. 2E are block diagrams that illustrate a finite element for predicting properties of a nucleic acid structure, according to one embodiment;

FIG. 4I is a table of example schematic model representations and example finite element model representations of various topological motifs, according to an embodiment;

FIG. 6B is a block diagrams that illustrates example alignment elements of a finite element model, used to characterize misalignments in non-final configurations, according to an embodiment;

FIG. 9A is a flow diagram that illustrates an example method for determining off-lattice 3D structure of a nucleic acid nanostructure, according to an embodiment;

FIG. 9B is a flow diagram that illustrates an example method for determining a directed graph from sequence data for duplexes, according to an embodiment;

FIG. 10 is a flow diagram that illustrates an example method for fabricating a nucleic acid nanostructure with controlled properties, according to an embodiment;

FIG. 11A is a block diagram that illustrates example dependence of 3D structure on values of certain parameters, according to an embodiment;

FIG. 11B is a block diagram that illustrates example truth table for the 3D structure of FIG. 11A, according to an embodiment;

DETAILED DESCRIPTION

Figure 1A:
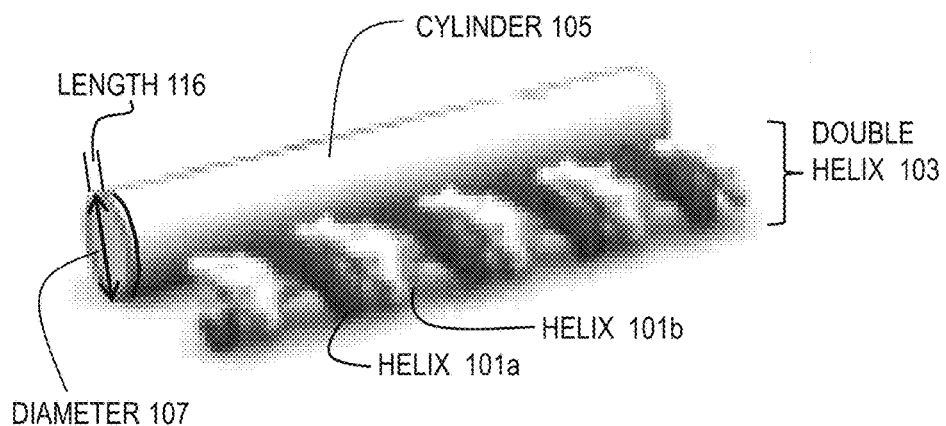
FIGS. 1A and 1B are block diagrams that illustrate multiple example representations of a portion of a DNA molecule, according to an embodiment.

A method, system, article of manufacture and apparatus are described for controlling mechanical properties of nucleic acid structures based on lattice-free, three dimensional junction coordinates. Topologically closed DNA structures make up an important class of nanostructures and can now be treated by the approach described herein, whereas they could not be treated by the previous approaches. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about x" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Deoxyribonucleic acid (DNA) is a replicating, usually double-stranded long molecule that encodes other shorter molecules, such as proteins, used to build and control all living organisms. DNA is composed of repeating chemical units known as "nucleotides" or "bases." There are four bases: adenine, thymine, cytosine, and guanine, represented by the letters A, T, C and G, respectively. On double stranded molecules, adenine on one strand of DNA always pairs with thymine on the other strand of DNA; and guanine on one strand always pairs with cytosine on the other strand and such bonded pairs are called base pairs. Any order of A, T, C and G is allowed on one strand, and that order determines the complementary order on the other strand. The actual order may determine the effect of that portion of the DNA molecule. Information on a portion of one strand of DNA can be captured by ribonucleic acid (RNA) that also comprises a chain of nucleotides in which uracil (U) replaces thymine (T). A portion of length k bases of a strand is called a k-mer; and specific short k-mers are called oligonucleotides or oligomers or "oligos" for short.

Some embodiments of the invention are described below in the context of scaffolded DNA origami comprising B-form double helix structures with one or more immobile four-way junctions, also called Holliday junctions, modeled using a finite element numerical model. Junctions can also more generally be multi-way junctions consisting of 3, 5, 6, 7, etc., DNA strands that intersect at a point joining multiple duplexes, as described below. However, the invention is not limited to this context. In other embodiments the 3D structure and other properties are determined for single helix DNA or ribonucleic acid (RNA) helices, or some combination, with or without Holliday junctions or other junctions using finite element or other numerical models, such as finite difference numerical models. The proposed computational modeling framework may be applied to DNA/RNA structures that are internally stabilized mechanically using secondary small molecules such as synthetic nucleic acids, amino acids, etc., which are modeled using distinct physical properties in the finite element model. The computational framework uses physical modeling to predict DNA/RNA origami 3D structural properties (e.g., position and orientation of each base, and therefore position of each atom), which affects shape and bulk mechanical, electromagnetic, optical and binding properties. In some embodiments, this information is integrated with any one of a number of optimization algorithms that can be used with objective functions based on mechanics and other considerations such as financial cost of oligos in order to rationally design DNA/RNA-based nanostructures.

Figure 1B:
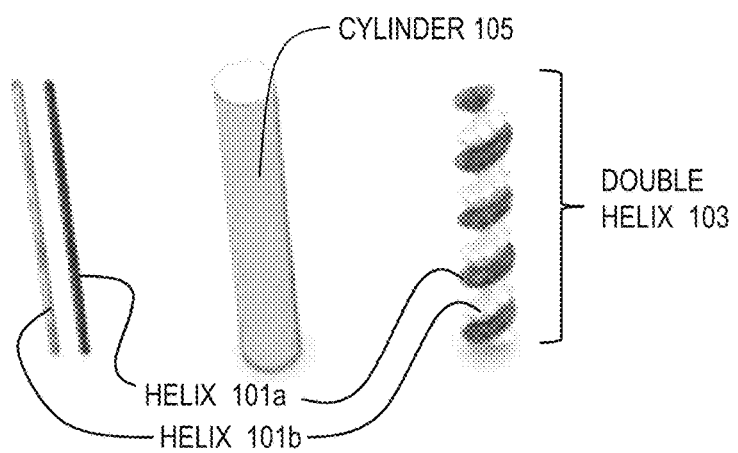

FIGS. 1A and 1B are block diagrams that illustrate multiple example representations of a portion of a DNA molecule, according to an embodiment. In FIG. 1A, a double helix structure 103 includes one strand of bases forming helix 101a and a second strand of bases forming helix 101b, all sharing the same central longitudinal axis. Though made up of the same nucleotides in complimentary sequences, helix 101a is rendered as dark in order to help visualize the spatial relationship between the two strands. The double helix 103 suggests a cylindrical volume, such as cylinder 105 with a diameter 107 and length that is a multiple of length 116 associated with the axial extent of one nucleotide. In a native configuration called B-form, one complete cycle of a helix around the axis corresponds to about 10.5 bases, e.g., two cycles corresponds to 21 bases. In FIG. 1B, the double helix 103 is depicted next to the cylinder 105. Also depicted is a linear representation in which the helix 101a and 101b are shown as parallel line segments, in essence a mental picture of the unwound strands of the double helix each offset equally from a central axis. For simplicity hereinafter the unwound helices depicted in linear representations are called strands; even though, in situ, these strands are shaped as helices.

Figure 1C:
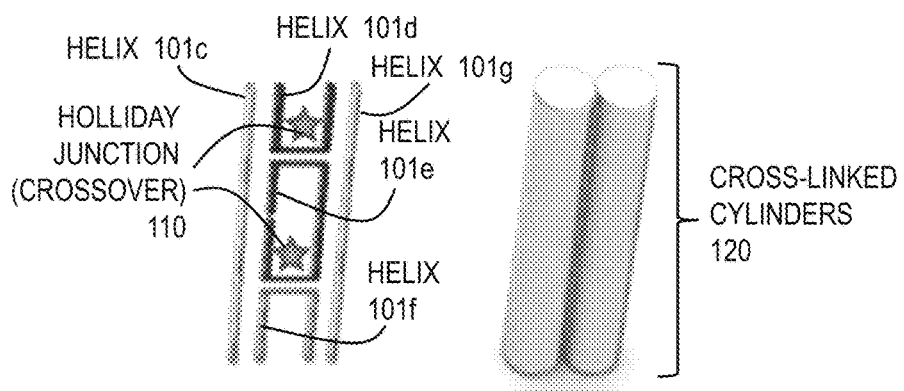
FIG. 1C is a block diagram that illustrates multiple representations of linked cylinders formed from one or more DNA molecules, according to an embodiment.

FIG. 1C is a block diagram that illustrates multiple representations of linked cylinders formed from one or more DNA molecules, according to an embodiment. The linkage is best understood in a schematic representation of unwound parallel strands. Five strands are shown that link two cylinders to form cross-linked cylinders 120. The top few bases of strand 101c are paired with corresponding bases on a first portion of strand 101d, but not with a second portion of strand 101d. That second portion of strand 101d has bases that pair with the top few bases of strand 101g. Similarly, the next few bases of strand 101c are paired with corresponding bases on a first portion of strand 101e, but not with a second portion of strand 101e. That second portion of strand 101e has bases that pair with the next few bases of strand 101g. The four strands 101c, 101d, 101e and 101g form a Holliday Junction 110, also called a crossover 110. The crossover 110 causes adjacent cylinders to be attached, e.g., cross-linked. Without a second crossover, however, the cross-linked cylinders might not be parallel to each other. A second Holliday junction 110 formed by strands 101c, 101e, 101f and 101g attaches the cross-linked cylinders 120 at a second location, and causes the cylinders to be parallel, at least in the vicinity of the two depicted Holliday junctions 110.

In one approach, the fundamental volume element for determining derived properties of nanoparticles constructed with scaffolded DNA origami is a Watson-Crick base pair comprising one nucleotide on one strand of a double helix bound to the complimentary nucleotide on the other strand. The base pair can be considered as a cylindrical disc with a diameter 107 of about 2.2 nanometers and a height of one nucleotide having length 116 of about 0.33 nanometers. FIG. 2A to FIG. 2E are block diagrams that illustrate a finite element for predicting properties of a nucleic acid structure, according to one embodiment. In the illustrated embodiments, there is one finite element for each base in a single strand or each base pair in a double strand. FIG. 2A is a block diagram that illustrates an example relationship between a single strand helix 101 and a finite beam element, according to one embodiment. For a single strand, represented by helix 101 with diameter 107 centered around axis 203, there is a node 205 corresponding to each nucleotide (base) located on an axis of the helix 101. There are 10.5 nodes in one complete turn of helix 101, represented by helix cycle length 209. The base or base pair is treated as a node connected by beam elements in a finite element model of the nanostructure.

In the illustrated embodiment, a finite element is a beam element 210 that extends from the center of one nucleotide node element (first base 212a) to the center of the next nucleotide node element (second base 212b). The beam position 214 is the midpoint of the beam; and the beam has beam length 116. In other embodiments, a finite element is a beam that extends from one end of one nucleotide to the opposite end of the same nucleotide on the same strand. The nucleotide is centered at the midpoint of the beam. In some embodiments of a finite element for a double helix, a finite element is a beam that extends from one end of one base pair linking the two strands to the opposite end of the same base pair. In each of these embodiments, the beam length 116 is the same.

FIG. 2B is a block diagram that illustrates an example spatial coordinate system for locating beams in a finite element model, according to an embodiment. The beam (e.g., base pair beam 210) has six degrees of freedom (DOF) and is located by three spatial coordinates for the center position 214 (e.g., three Cartesian coordinates or three polar coordinates) and the orientation of the beam is indicated by three angles relative to three coordinate axis directions. The orientation component 222 relative to one coordinate axis direction 220 is illustrated.

In any of these embodiments, the finite element is considered to be a beam with certain physical properties besides length 116. FIG. 2C is a block diagram that illustrates a bending spring constant $k_b$, according to an embodiment. The spring constant $k_b$ indicates the resultant change in beam curvature as the beam deflects in response to a bending moment 230 (as used herein a moment is a force applied at a distance, also called a torque) that does not rupture the material element represented by the beam. Bending can be in either or both of two directions perpendicular to the axis of the beam. FIG. 2D is a block diagram that illustrates a twisting spring constant $k_t$, according to an embodiment. The spring constant $k_t$ indicates the angle the beam twists in response to a twisting moment 240 that does not rupture the material element represented by the beam. The bending and twisting stiffness is called rotational stiffness hereinafter and represented by coefficient, such as a spring constant $k_r$, in each of one or more rotational DOF. FIG. 2E is a block diagram that illustrates a stretching spring constant $k_s$, according to an embodiment. The spring constant $k_s$ indicates the distance the beam extends (or contracts) along the axis in response to a positive (or negative) stretching force 250 that does not rupture the material element represented by the beam. The stretching and compression stiffness is called translational stiffness hereinafter and represented by coefficient, such as a spring constant $k_t$, in each of one or more translational DOF. In some embodiments, one or more coefficients are functions of the magnitude of rotation or translation or the nucleotides in the beam element or some other factor.

Figure 2F:
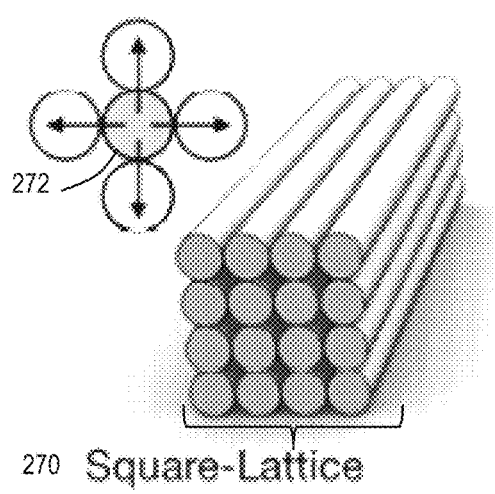
FIG. 2F and FIG. 2G are block diagrams that illustrate example lattices formed from one or more DNA molecules.
Figure 2G:
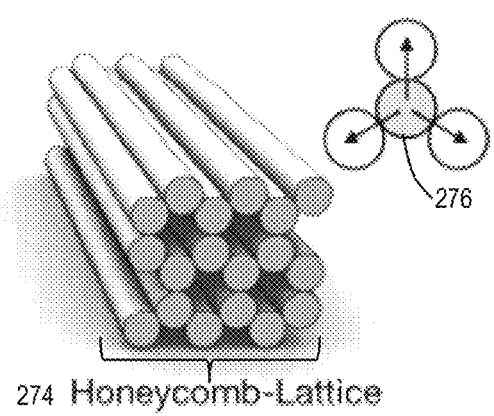

FIG. 2F and FIG. 2G are block diagrams that illustrate example lattices formed from one or more DNA molecules. FIG. 2F illustrates an example square lattice 270 in which each cylinder is cross linked at two or more Holliday junctions with each of four neighboring cylinders as indicated by insert 272. The four junctions, though displayed in one cross section, are actually located at different positions along the length of the cylinder. FIG. 1G illustrates an example hexagonal lattice 274 (also called a honeycomb lattice 274) in which each cylinder is cross linked at two or more Holliday junctions with each of three neighboring cylinders as indicated by insert 276. The three junctions, though displayed in one cross section, are actually located at different positions along the length of the cylinder.

1. Overview

Figure 3:
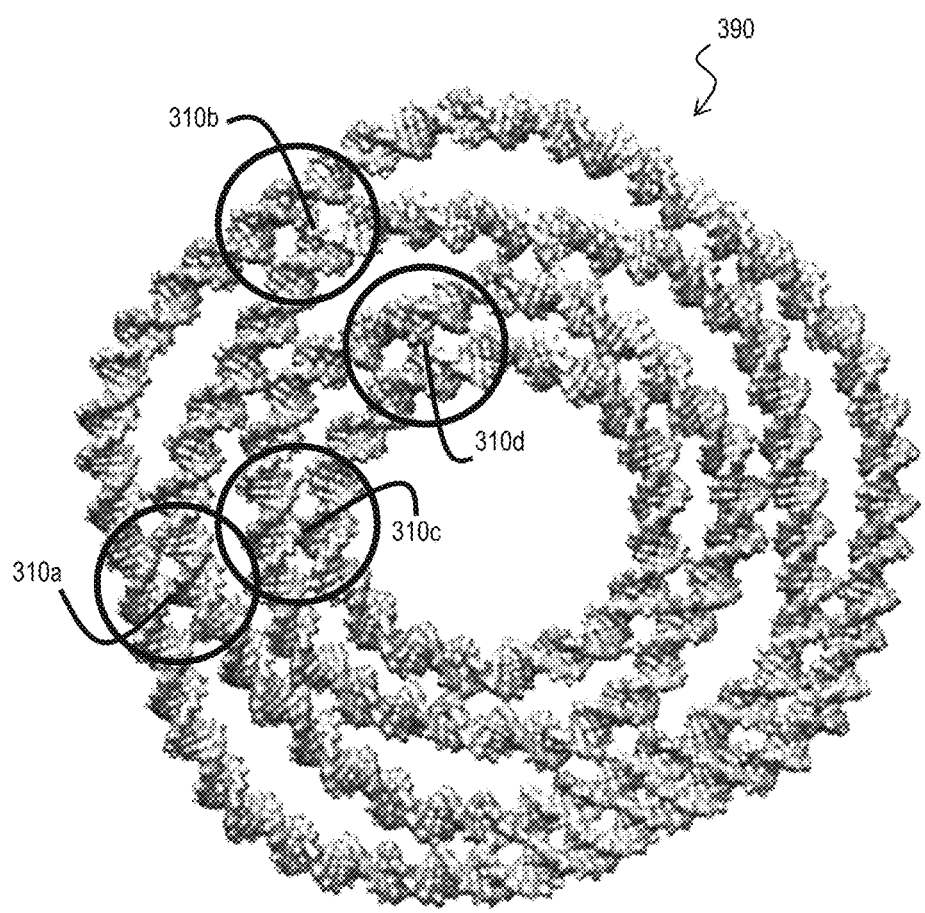
FIG. 3 is a block diagrams that illustrates an example DNA structure with off-lattice junctions, according to an embodiment.

The symmetries of the lattices depicted in FIG. 2F and FIG. 2G were used, in previous work, to specify the location of junctions and the stresses and deformations those junctions introduce to the nanostructure. However, junctions in many nanostructures do not readily map to the lattice coordinates. FIG. 3 is a block diagram that illustrates an example DNA structure with off-lattice junctions, according to an embodiment. In this 4 ring nanostructure 390 in which individual bases are represented as gray spheres, junctions 310a, 310b, 310c and 310d (collectively referenced hereinafter as junctions 310) are located at centers of the circles drawn to aid in identifying the junctions. Lattices of parallel cylinders are not suited for locating these junctions and simplifying the computation of deformations. Thus, in various embodiments, nanostructures with junctions are modeled using different reference frames, called off-lattice reference frames or off-lattice coordinates or simply 3D coordinates, hereinafter. Furthermore, junctions are not limited to Holliday junctions in the embodiments described below.

Figure 4A:
FIG. 4A through FIG. 4H are block diagrams that illustrate multiple example helix and junction types (motifs), according to an embodiment.

FIG. 4A through FIG. 4H are block diagrams that illustrate multiple example helix and junction types (motifs), according to an embodiment. Similarly, other motifs are included in other embodiments. FIG. 4A shows two strands of a DNA dual helix, called herein a duplex. The arrowhead points in the 5' to 3' direction for each strand to emphasize that the paired strands are oriented in opposite directions. The double helix structure of DNA contains a major groove and minor groove, the major groove being wider than the minor groove. Given the difference in widths of the major groove and minor groove, many proteins which bind to DNA do so through the wider major groove. The most common form of the DNA duplex is the B-form. In B-form DNA (also signified as B-DNA), the double helix is right-handed with about 10-10.5 nucleotides per turn. A-form DNA (also signified as A-DNA) is a right-handed double helix fairly similar to B-DNA, but with a shorter more compact helical structure. A-DNA is possibly assumed by DNA-RNA hybrid helices and the same geometrical conformation is commonly seen in double-stranded RNAs. Z-form DNA (also signified as Z-DNA) is a left-handed double helical structure in which the double helix winds to the left in a zig-zag pattern. The different rest geometries of the three forms are summarized in Table 1.

TABLE 1

Ground-state geometry of duplexes.

| Geometric attribute | A-form | B-form | Z-form |
| --- | --- | --- | --- |
| Helix sense | Right-handed | Right-handed | Left-handed |
| Repeating unit | 1 bp | 1 bp | 2 bp |
| Rotation per repeating unit | 33.6° | 35.9° | 60° |
| Mean bp per turn | 11 | 10.5 | 12 |
| Inclination of bp to axis | 19° | −1.2° | −9° |
| Rise per bp along axis | 0.24 nm | 0.34 nm | 0.37 nm |
| Diameter | 2.3 nm | 2.0 nm | 1.8 nm |

(where bp = base pair, nm = nanometer, 1 nm = $10^{-9}$ meters))

For B-DNA, the stretch modulus 1,100 pN, bend modulus 230 pN $nm^2$, and twist modulus 460 pN $nm^2$ of the beam are set to their experimental values.

Figure 4B:
Figure 4C:
Figure 4D:
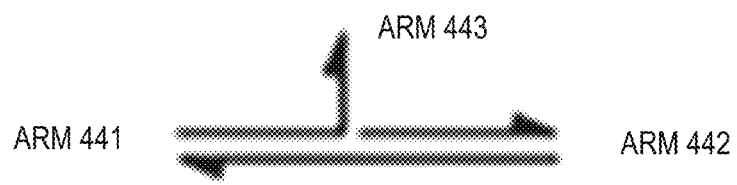

FIG. 4B shows two strands of a nicked DNA duplex. A nick is a discontinuity in a double stranded DNA molecule where there is no phosphodiester bond between adjacent nucleotides of one strand typically through damage or enzyme action. Nicks allow for the release of torsional and bending moments when critical loading is exceeded at the nick position, and thus a helix with a nick has a different mechanical response to bending and twisting that can be modeled as rupture or reduced stiffness or bilinear stiffness, with corresponding coefficient values. Nicks in double-stranded DNA (dsDNA) are modeled by the same beam elements with either identical or reduced bend and twist moduli or a rupture criterion that reduces the torsional and bending moments to zero at a critical load. FIG. 4C shows two strands of a gapped DNA duplex in which one or more bases complementary to a continuous (e.g., the bottom) strand are missing. FIG. 4D shows a single stranded DNA overhang. An overhang is a stretch of unpaired nucleotides in a DNA molecule, either at the end of strand, or, as shown, in the middle adjacent to a nick or gap. These unpaired nucleotides can be in either strand, creating either 3' or 5' overhangs. The depicted arrangement results in a junction with three arms 441, 442 and 443, of which arm 443 is single stranded. FIG. 4D is one example of a three way junction; and, is also a motif for a crossover between two duplexes, in which case the crossover has zero rotational stiffness and no preferred ground-state angle. In some embodiments, a three-way junction is formed by pairing the overhang in arm 443.

Figure 4E:
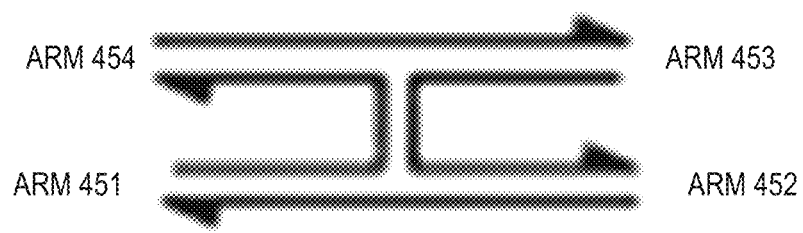
Figure 4F:
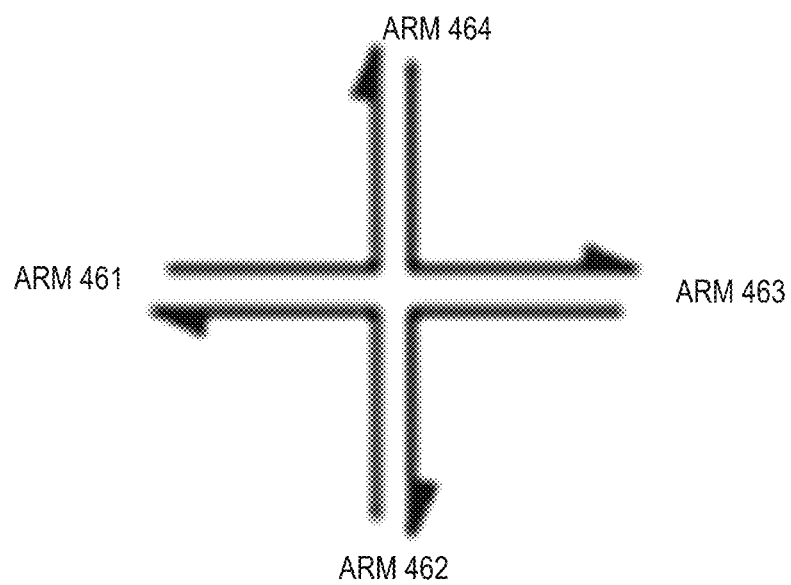
Figure 4G:
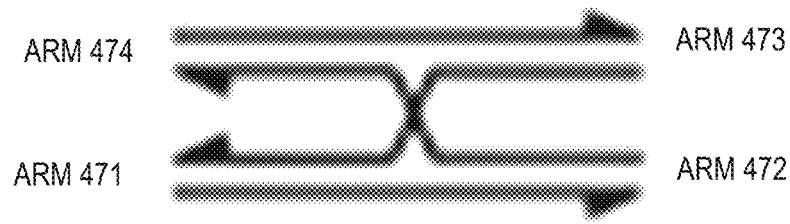
Figure 4H:
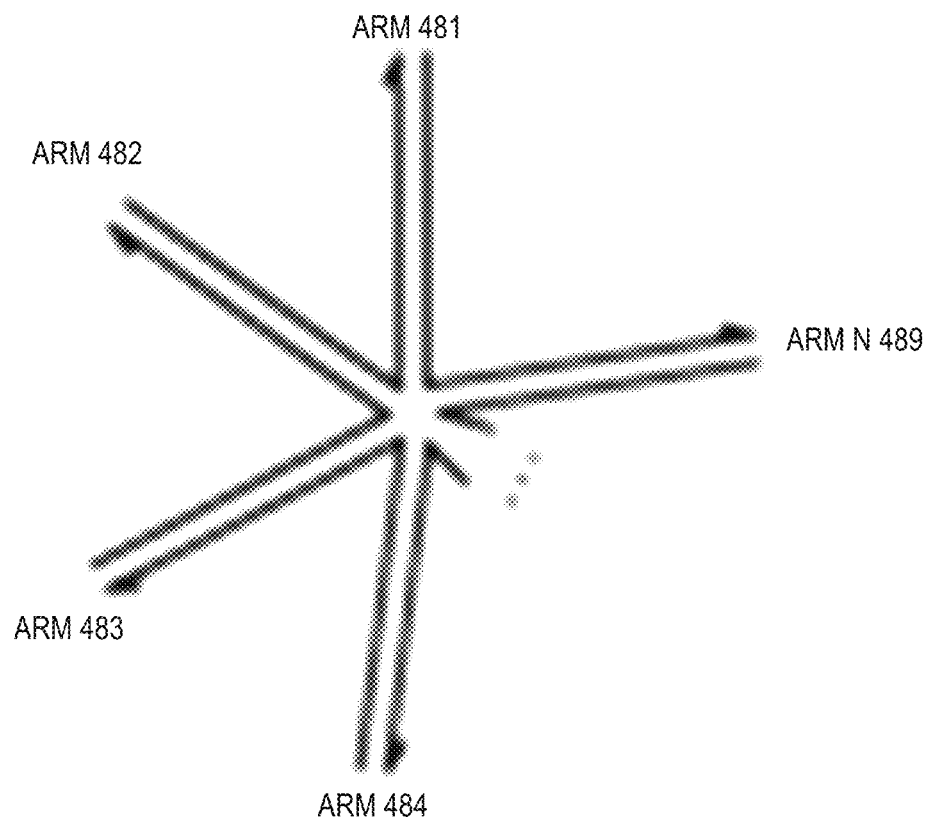

Example configurations of four-way junctions at high Magnesium concentration (>2 mM) are shown in FIGS. 4E and 4G. The four-way junction at these Magnesium concentrations adopts either a parallel or anti-parallel configuration with a ground-state, equilibrium scissor angle between the duplexes that is approximately 40 to 60 degrees (°) but depends on the specific DNA sequence at the junction point. FIG. 4E depicts an antiparallel, stacked, four-way junction in which the non-crossing strands are in opposite directions. A Holliday junction is a mobile antiparallel, stacked four-way junction, which means the position of the junction can migrate. On the other hand, most four-way junctions implemented in DNA nanotechnology are immobile (position of junction is fixed). FIG. 4G depicts a parallel, stacked, four-way junction in which the non-crossing strands are in the same direction. FIG. 4F depicts an open-X configuration of the four-way junction that is adopted at low Magnesium concentration (<5 microMolar, μM, 1 μM=$10^{-6}$ Molar). The flexible four-way junction only occurs at low Magnesium concentration, and therefore to generalize this flexible four-way junction to any number of arms flexibly joined, a poly-T intervening sequence is inserted between nearest-neighboring duplexes in the N-way junction, where N is greater than or equal to 3. For example, FIG. 4H depicts an N-way junction that includes arms 481, 482, 483 484 and zero or more intervening arms indicated by the ellipsis and ending on the N-th arm 489.

FIG. 4I is a table of example schematic model representations and example finite element model representations of various topological motifs, according to an embodiment. As depicted in the first row, a B-form duplex of N base pairs comprises two stands in the schematic model, with N bases in each strand; and N finite element nodes connected by N−1 beam elements in the finite element model. As depicted in the second row, a nick (indicated by the broken circle in the first and last columns) in a duplex comprises a broken strand in the schematic model but with no missing bases ($N_1$=0, where $N_1$ represents the number of missing bases on a strand); and a modified (e.g., softened) beam elements in the finite element model. As depicted in the third row, a gap (indicated by the broken oval in the first and last columns) in a duplex comprises missing bases in one strand in the schematic model, where $N_1$ has a value from 1 to less than $N_{SS}$, where $N_{SS}$ is a minimum number of missing bases in a single-stranded region, typically about 5, so that less than half of a helical turn is missing in a gap. A gap is represented by a truss element connecting two finite element nodes in the finite element model. A truss (spar) element is a subset of beam-type elements, which can't carry moments (i.e., have no bending DOF's). These are commonly called "two-force members", carrying only axial load. As depicted in the fourth row, a single-stranded region (indicated by the broken oval in the first and last columns) in a duplex comprises a broken strand in the schematic model with $N_{SS}$ or more missing bases, so that at least half a helical turn is single-stranded; and a different truss element in the finite element model. As depicted in the fifth row, a bulge (indicated by the broken circle in the first and last columns) in a duplex comprises one or more extra unpaired bases in one strand in the schematic model ($N_2$>0, where $N_2$ represents the number of extra unpaired bases on a strand); and a modified (e.g., softened) beam elements in the finite element model.

Figure 4J:
FIG. 4J is a table of example schematic model representations and example finite element model representations of various junction topological motifs, according to an embodiment.

FIG. 4J is a table of example schematic model representations and example finite element model representations of various junction topological motifs, according to an embodiment. As depicted in the first row, an isolated phosphodiester bond (indicated by the broken circle in the first column) comprises three strands in the schematic model; and an alignment element between two beam nodes in the finite element model. Alignment elements are described in more detail below. As depicted in the second row, a double crossover (indicated by the broken circle in the first column) comprises four strands in the schematic model; and two alignment elements between four beam nodes in the finite element model. As depicted in the third row, a single crossover (indicated by the broken circle in the first column)

comprises four strands in the schematic model of which one has a nick or gap; and two alignment elements between four beam nodes in the finite element model.

Figure 5A:
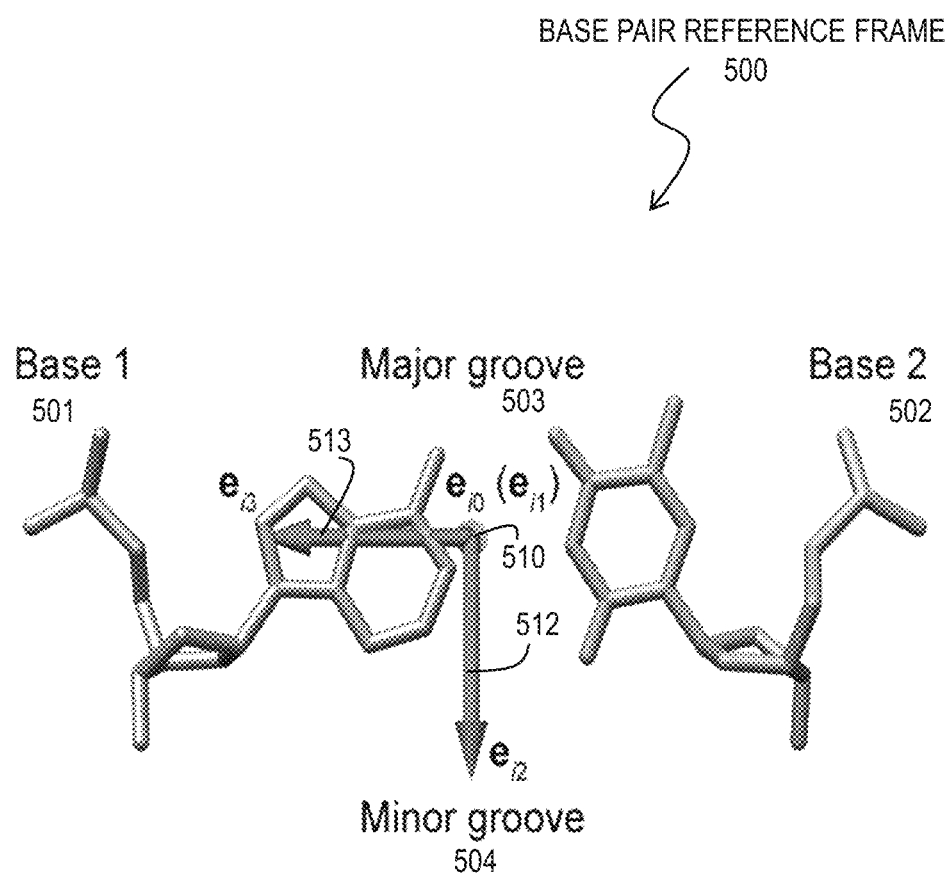
FIG. 5A through FIG. 5F are block diagrams that illustrate example off-lattice reference frames for base pairs and a Holliday junction, according to an embodiment.

FIG. 5A through FIG. 5F are block diagrams that illustrate example off-lattice reference frames for base pairs and a Holliday junction, according to an embodiment. FIG. 5A depicts a relative reference frame 500 for the i-th base pair according to the 3DNA convention. The relative reference frame for base pair comprising base 501 and base 502 has an origin $e_{i0}$ 510 between the bases, and an orientation given by basis vector $e_{i1}$ (perpendicular into the plane of FIG. 5A) directed along the axis of the helix, a basis vector $e_{i2}$ 512 perpendicular to $e_{i1}$ and directed from the major groove 503 toward the minor groove 504, and a basis vector $e_{i3}$ 513 perpendicular to both $e_{i1}$ and $e_{i2}$ using a right-hand rule and directed toward a sugar backbone of the helix for one of the bases. The coordinates for $e_i$ and the tips of the basis vectors $e_{i1}$, $e_{i2}$, $e_{i3}$ can be expressed in coordinates of an absolute 3D reference frame.

Figure 5B:
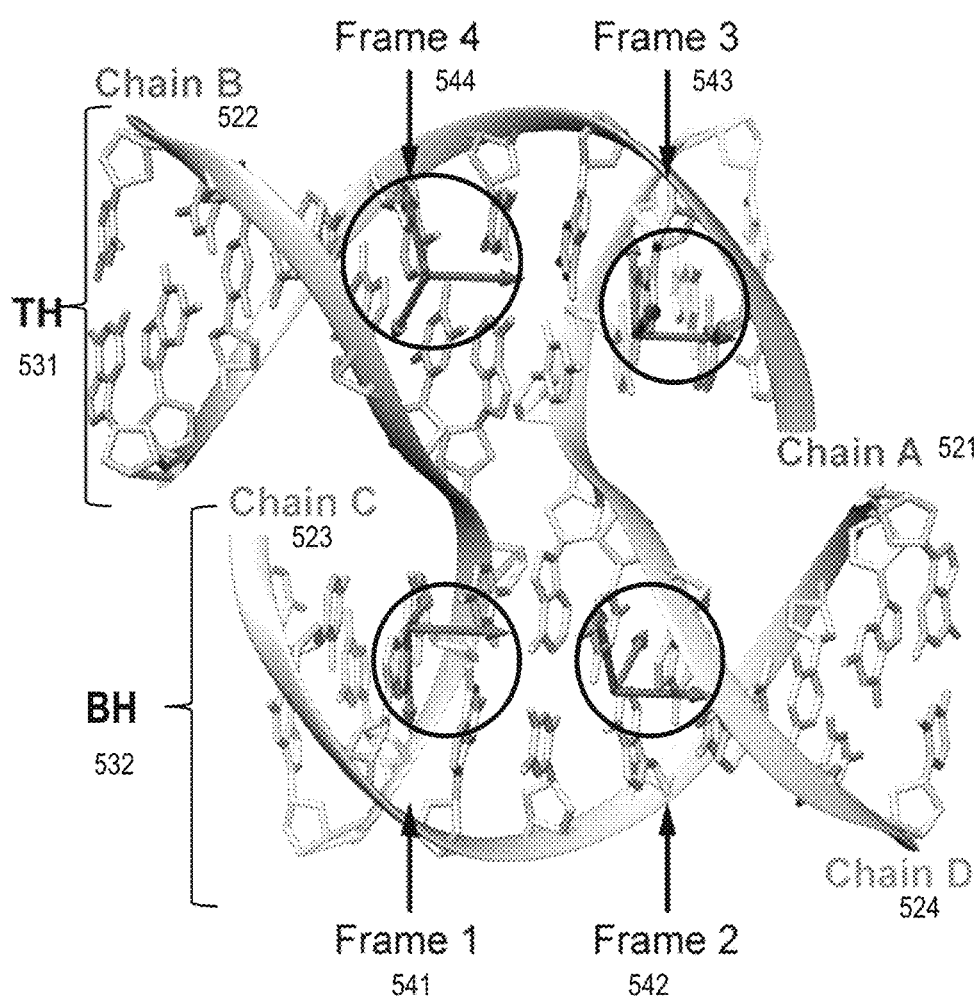
Figure 5C:
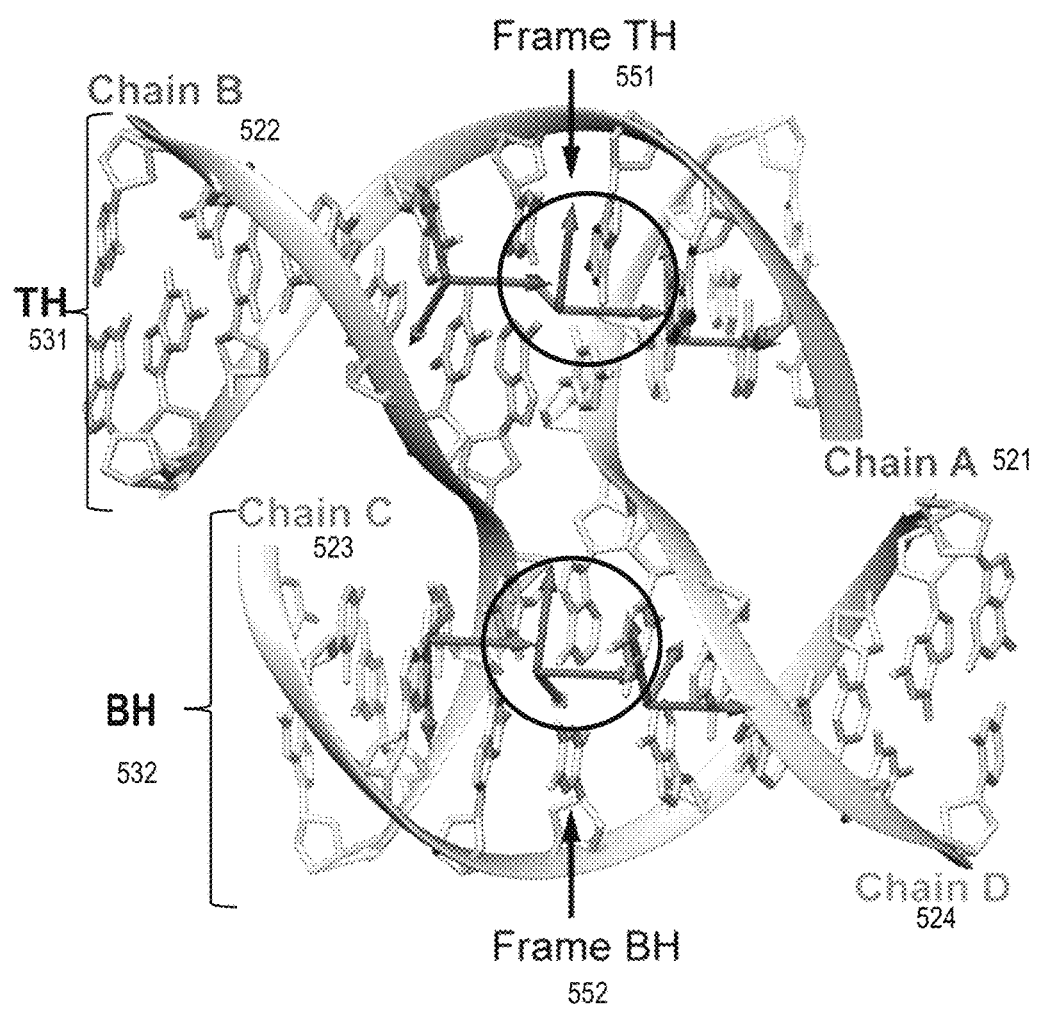
Figure 5D:
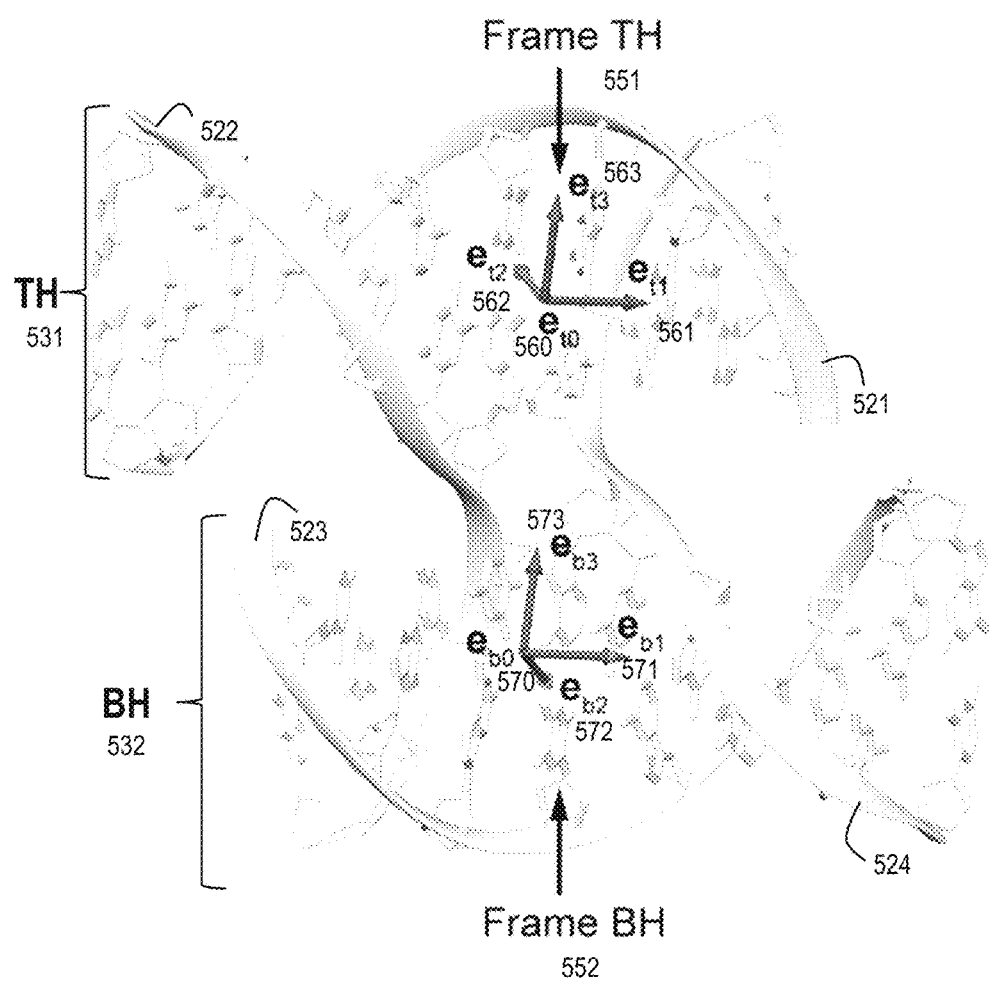

FIG. 5B depicts atomic positions for atoms in the nucleotides of an antiparallel, stacked four-way junction that involves four strands labeled chain A 521, chain B 522, chain C 523 and chain D 524. An arbitrarily chosen duplex, for convenience called a top helix designated TH 531, includes non-crossing chain A 521. The other duplex, for convenience called a bottom helix designated BH 532, includes non-crossing chain C 523. Four base pairs flank the crossover point, and their relative reference frames constitute frame 1 541, frame 2 542, frame 3 543, and frame 4 544, respectively, each circled in FIG. 5B. FIG. 5C depicts a reference frame for the bottom helix, designated Frame BH 552, based on averaging the coordinates and orientations of frame 1 541 and frame 2 542. Similarly, FIG. 5C depicts a reference frame for the top helix, designated Frame TH 552, based on averaging the coordinates and orientations of frame 3 543 and frame 4 544. Frame BH 552 and Frame TH 551 are circled for convenience. FIG. 5D shows the components of the Frame TH 551 as $e_{t0}$ 560, $e_{t1}$ 561, $e_{t2}$ 562, $e_{t3}$ 563; and, the components of Frame BH 552 as $e_{b0}$ 570, $e_{b1}$ 571, $e_{b2}$ 572, $e_{b3}$ 573. The atomistic structure of the junction is thus represented in coarse-grain as two rigid bodies represented by frames BH and TH, respectively.

Figure 5E:
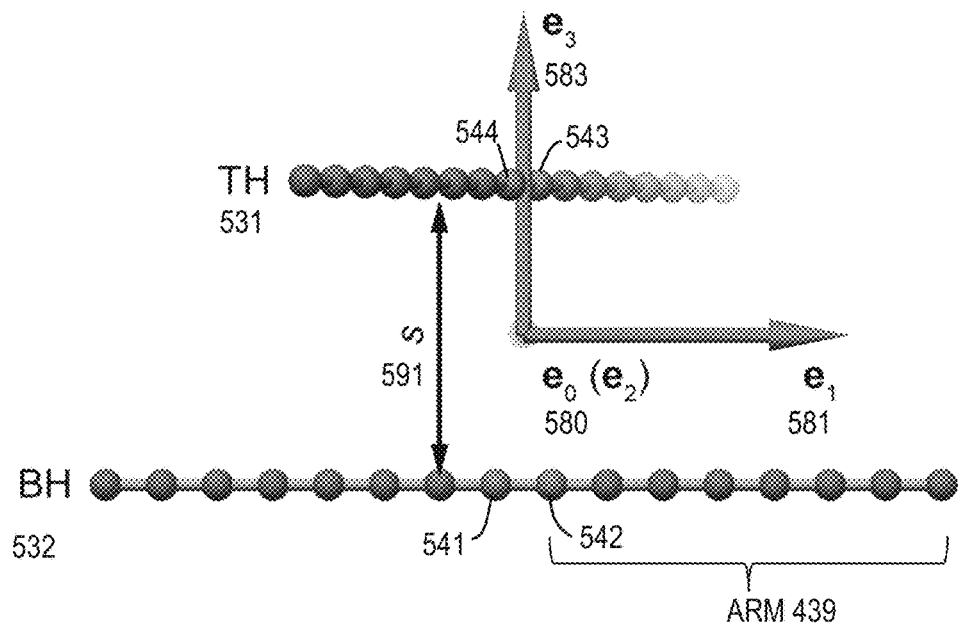
Figure 5F:
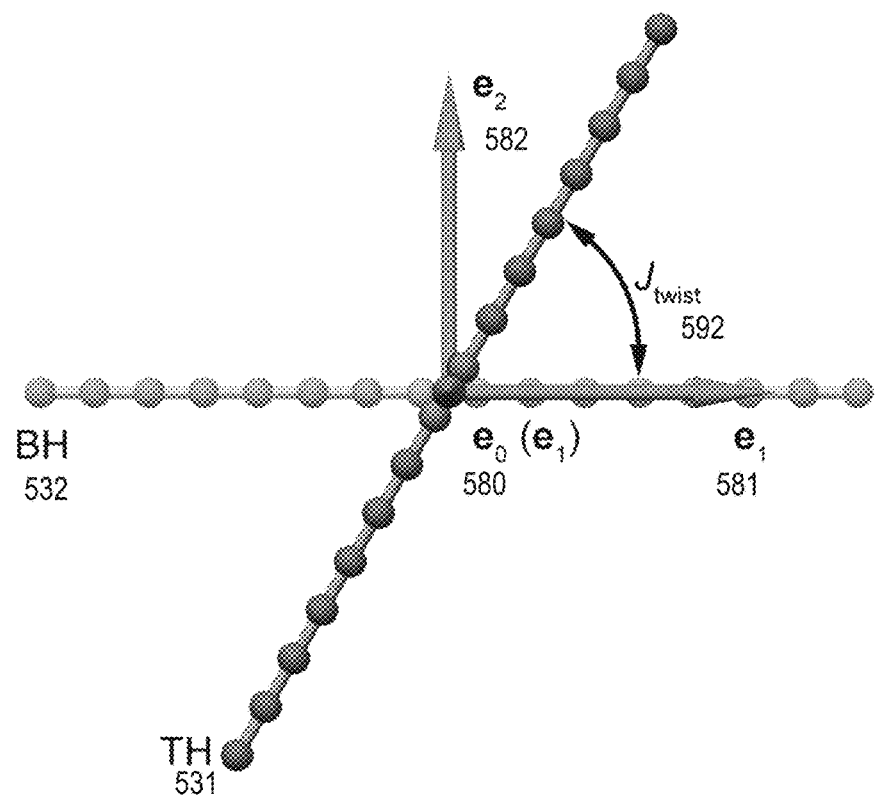

A reference frame for a junction is then obtained by the average of the origins and basis vectors of the joined duplexes. In the illustrated embodiment, the antiparallel, stacked four-way junction has a reference frame with origin at $e_0$ based on the average of $e_{t0}$ and $e_{b0}$. By convention, without loss of generality, the basis vector $e_1$ is taken parallel to the bottom helix $e_{b1}$ and thus the basis vectors $e_2$ and $e_3$ are parallel to $e_{b2}$ and $e_{b3}$, respectively. FIG. 5E depicts the TH 531 and BH 532 as viewed in direction $e_2$, with each base pair depicted as a sphere. The four base pairs that defined frames 1 through frame 4 are indicated as nodes 541, 542, 543 and 544. Junction origin $e_0$ 580 and orientations $e_1$ 581 and $e_3$ 583 are shown. Extending from the junction center $e_0$ 580 along one duplex is an arm 439. TH 531 and BH 532 are separated by an inter-helical distance s 591. FIG. 5F depicts the TH 531 and BH 532 as viewed in direction $-e_3$, with each base pair depicted as a sphere. Junction origin $e_0$ 580 and orientations $e_1$ 581 and $e_2$ 582 are shown. TH 531 and BH 532 are separated by an inter-helical angle $J_{twist}$ 592. As described in more detail below with reference to an illustrated embodiment, the ground-state geometry value of s is about 1.85 nm and the ground-state geometry value of $J_{twist}$ is in a range from about 40° to about 60°. In an illustrated embodiment, described in more detail below, the rest value of $J_{twist}$ is taken to be 60° based on experiments. In other embodiments, other values can be used.

Just as coefficients of bending, twisting and compression were determined for individual bases in a single or double helix, depicted in FIG. 2C through FIG. 2E, so too are stiffness coefficients determined for translational and rotational perturbations of each junction type. This can be done by simulation or experimentation or some combination. For example, based on simulations and experiments described below for an illustrated embodiment, the stiffness coefficients for the antiparallel, stacked four-way junction are determined as listed below in Table 2. Similarly, the ground-state geometry values for the position and orientation of other junction types can be determined, as can the stiffness coefficients for translational and rotational perturbations about the ground-state geometry. With sufficient information, the coefficients can be functions of the perturbation size or nucleotide base or other factors in some embodiments. For purposes of illustration, the stiffness coefficients are assumed to be constant in the illustrated embodiments.

The ground-state geometry and stiffness coefficients for translational and rotational perturbations for the above types of helices and junctions, as well as other types of helices and junctions, can be obtained from the published literature or through experimentation or simulation, or some combination, as described for a four-way junction in more detail below. Example values are presented below in Table 2, in which translational stiffness coefficients are given in picoNewtons (pN, 1 pN=$10^{-12}$ newtons) per nanometer (nm) and rotational stiffness coefficients are given in pN nm per radian of rotation. The open four-way junction only occurs at low salt unless poly-TTT is inserted between neighboring arms, when, like with all N-way junctions, it becomes fully flexible with no preferred ground-state relative angles and no stiffness associated with any rotational DOF. This is modeled as "pivots" that are fully flexible in rotation between arms in this model for any N-way junction (only the number of arms changes). Table 2A provides values for parameters of mechanical models for the topological motifs depicted in FIG. 4I.

TABLE 2A

Example values for geometry and stiffness coefficients (mechanical models) of various types of helices from FIG. 4I.

| | Topological motif | | | | |
|---|---|---|---|---|---|
| | Duplex (beam) | Nick (beam) | Gap (freely-jointed chain) | Single-stranded region (freely-jointed chain) | Bulge (beam) |
| Axial rise per base pair (nm) | 0.34 | 0.34 | | | 0.34 |
| Right-handed twist per base pair (°) | 360/10.5 | 360/10.5 | | | 360/10.5 |

TABLE 2A-continued

Example values for geometry and stiffness coefficients (mechanical models) of various types of helices from FIG. 4I.

| | Topological motif | | | | |
|---|---|---|---|---|---|
| | Duplex (beam) | Nick (beam) | Gap (freely-jointed chain) | Single-stranded region (freely-jointed chain) | Bulge (beam) |
| Stretch modulus (pN) | EA = 1100 | EA = 1100 | S = 800 | S = 800 | EA = 1100 |
| Bend modulus (pN nm$^2$) | EI = 230 | EI = 230 | | | EI = 2.30 |
| Twist modulus (pN nm$^2$) | GJ = 460 | GJ = 460 | | | GJ = 4.60 |
| Contour length, L, per base pair (nm) | | | 0.5 | 0.5 | |
| Kuhn length, b (nm) | | | 1.5 | 1.5 | |
| Entropic elasticity, R | | | Per Equation. | Per Equation. | |

Where Entropic elasticity R is given by the Equation:

$$R = L[coth(Fb/k_BT) - k_BT/Fb](1+F/S)$$

where b is Kuhn length, S is stretch modulus, F is the axial force in the truss modeling the freely-jointed chain polymer, $k_B$ is the Boltzmann constant, and T is temperature. Table 2B provides values for parameters of mechanical models for the junction topological motifs depicted in FIG. 4J.

TABLE 2B

Example values for geometry and stiffness coefficients (3 DOF torsional spring, mechanical model) of various types of non-four-way junctions from FIG. 4J.

| Topological motif | Inter-helical distance, s (nm) | Interhelical angle about e3, $J_{twist}$ (°) | Translational stiffness coefficients, kt (pN/nm) | Rotational stiffness kr (pN nm/rad) |
|---|---|---|---|---|
| Isolated phosphodi-ester bond | 1.85 | 0 | 6.47 × 10$^6$ | $kr_1, kr_2 = 0$<br>$k_{twist} = 0$ |
| Double crossover | 1.85 | 0 (DX tiles);<br>180 (PX tiles);<br>60 (others) | 6.47 × 10$^6$ | $kr_1, kr_2 = 1353$<br>$k_{twist} = 135.3$ |
| Single crossover | 1.85 | 0 | 6.47 × 10$^6$ | $kr_1, kr_2 = 0$<br>$k_{twist} = 0$ |

Thus is determined, for each junction type of one or more nucleic acid junction types, a plurality of values corresponding to a plurality of fixed parameters that indicate a ground-state geometry and translational and rotational junction stiffness coefficients for perturbations from the ground-state geometry.

According to various embodiments, the base sequence design of a nucleic acid nanostructure is analyzed to determine the junctions and connecting helices. Any sequence design data format can be used. For example, in various embodiments, design data are in files in Tiamat format (see, Williams S, et al. (2009) Tiamat: A three-dimensional editing tool for complex DNA structures. *DNA* 14, pp 90-101). For each junction the junction type is determined, and for each helix the helix type and number of bases is determined, in order to determine the ground-state geometry and stiffness coefficients applicable to each.

For example, the base sequence design, in a design data set, is analyzed as a directed graph with the bases (or base pairs) forming nodes, helices indicate by nodes with two edges and the junctions indicated by nodes with edges connected to different helices. A graph algorithm identifies all junctions together with the helix arm lengths intervening them. The graph algorithm also determines the identity of each nucleotide base in each arm, and connectivity between nucleotide bases. Any directed graph routine may be used.

The directed graph is used to organize the assembly of the nanostructure in a structural model of the nanostructure, such as in a finite element model. Thus is obtained, or otherwise determined, design data that indicates, for a nucleic acid structure, a number of nucleic acid bases in each helix of a set of two or more helices, wherein the set of helices are joined at a corresponding junction, for a plurality of sets of helices in the nucleic acid structure, wherein the plurality of sets of helices are connected by a plurality of junctions.

Figure 6A:
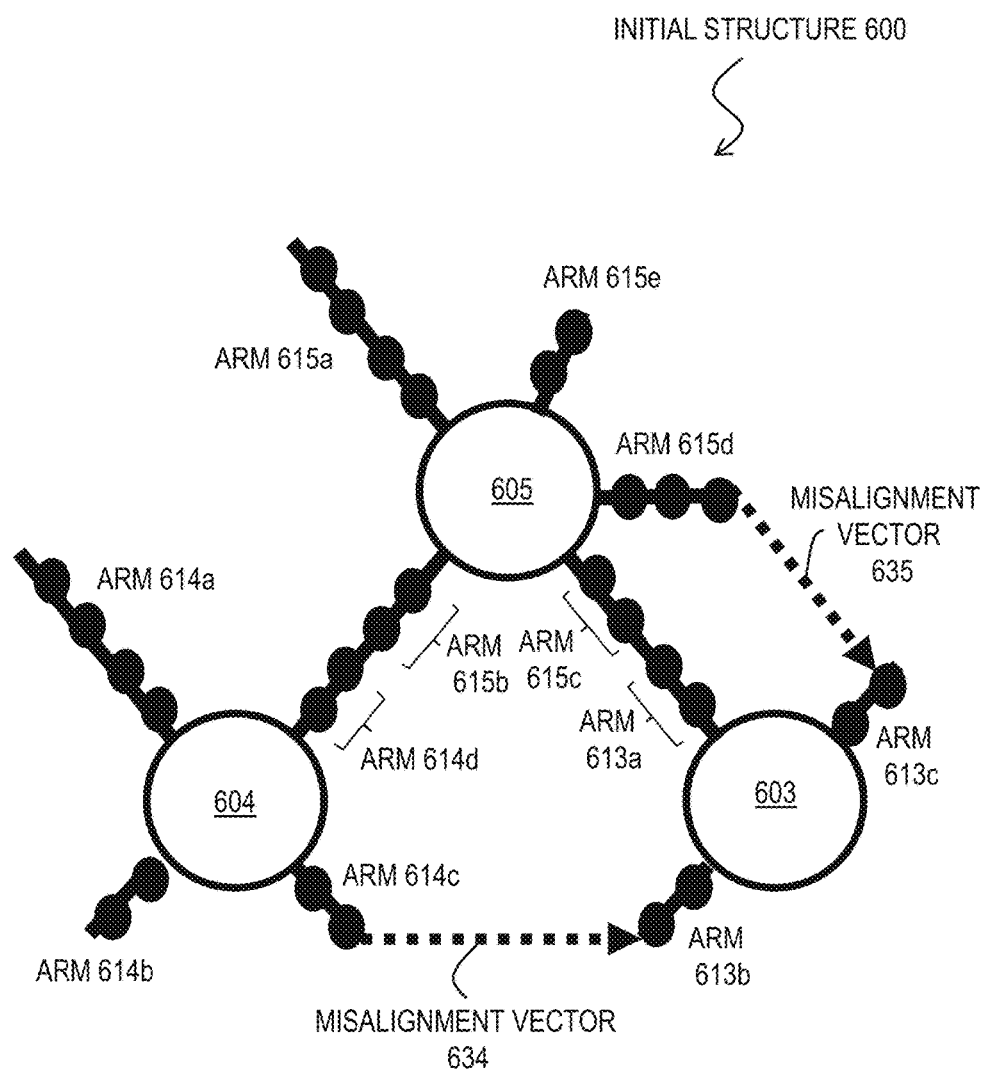
FIG. 6A is a block diagram that illustrates an example initial structure obtained by connecting helices and junctions in rest configuration, according to an embodiment.

According to the illustrated embodiments, the nanostructure is given an initial configuration, e.g., in a finite element model, by adding each helix to each junction, according to the directed graph, with each junction and helix having its ground-state geometry. At the end of this process there are gaps in the initial configuration of the structure where the ends of several rest geometries do not line up. FIG. 6A is a block diagram that illustrates an example initial structure 600 obtained by connecting helices and junctions in rest configuration, according to an embodiment. Three junctions include an open three-way junction 603, an open four-way junction 604, and an open 5 way junction 605, each indicated by an open circle. Connected to each junction are one or more arms of helices with a base (or base pair) indicated by a solid circle. In the illustrated example, junction 603 is connected to arms 613a, 613b, 613c with two nucleotide bases per arm. Similarly, junction 604 is connected to a four nucleotide base arm 614a and two nucleotide base arms 614b, 614c, 614d. Similarly, junction 605 is connected to four nucleotide base arm 615a, three nucleotide base arm 615d and two nucleotide base arms 614b, 614c, 614e.

The arms extend from the junctions at the angles corresponding to the ground-state geometry for that junction type. Arm 615b of junction 605 is connected to arm 614d of junction 604 using the ground-state geometry of a helix of the types of arms 615b and 614d. Similarly, arm 615c of junction 605 is connected to arm 613a of junction 603 using the ground-state geometry of a helix of the types of arms 615c and 613a. Each junction and base is allowed to take up any coordinate in 3D space and is not confined to lattice coordinates, as in some prior approaches. Although the design data indicates that arm 614c of junction 604 also connects to arm 613b of junction 603 (and thus the terminal node on each arm refers to the same base or base pair), the ground-state geometry does not allow that connection. The misalignment is indicated by misalignment vector 634, not only by the difference in location of the ends of the two arms, but also by the difference in orientation of the two arms. Similarly, although the design data indicates that arm 613c of junction 603 also connects to arm 615d of junction 605, the ground-state geometry does not allow that connection. The misalignment is indicated by misalignment vector 635. Note that arm 613b of junction 603 could have been placed with ground-state geometry at the end of arm 614c of junction 604. In such a case, the misalignment vector 634 would move to a gap created, instead, between arm 613a and 615; and, misalignment vector 635 would have different magnitudes in the 6 DOF.

Thus is determined, initial positions of each base in the nucleic acid structure by connecting helices at junctions using the ground-state geometry of each junction, wherein the initial positions are in arbitrary three dimensional coordinates that are not confined to lattice coordinates. Also thus determined is a set of one or more misalignment vectors, wherein each misalignment vector indicates a difference in three dimensional coordinates between initial positions of a pair of bases that are not adjacent in the initial positions but are adjacent in the design data.

As described below, this misalignment is eliminated or otherwise reduced by applying forces or moments or both to bring the two arms into connection at the same orientation and balancing the forces and moments throughout the rest of the components of the structure. The forces and moments propagated to the other components cause each to be perturbed in some combination of translational and rotational directions by amounts related to their translational and rotational stress coefficients. Forces and moments at junctions balance forces and moments in helices. A junction can deviate from its rest state if it adds twist to a helix between adjacent junctions. After reducing or eliminating all the misalignment magnitudes so the structure is in static equilibrium, the resulting three dimensional structure indicates position and orientation of each base in the 3D coordinates not confined to the lattices of the prior work, and thus the position of each atom in the nucleic acid nanostructure is determined.

Thus, forces and moments at the plurality of junctions are determined to reduce magnitudes corresponding to the set of misalignment vectors based on the set of misalignment vectors and the translational and rotational junction stiffness coefficients at each junction of the plurality of junctions. A three dimensional structure comprising position and orientation in three dimensional coordinates of each base in the nucleic acid structure is thus determined by reducing, including eliminating, the magnitudes corresponding to the set of misalignment vectors and balancing forces and moments across the nucleic acid structure. For example, in various embodiments, the resulting structural model is output as atomistic models in Protein Data Bank (PDB) format. This format is available on the World Wide Web at domain rcsb of super domain org as file home.do in folder pdb and subfolder home (see Bernstein, F. C; Koetzle, T. F.; Williams, G. J. B.; et al. "Protein Data Bank—Computer-Based Archival File For Macromolecular Structures" *Journal Of Molecular Biology* Volume: 112 (3) pp535-542, 1977).

FIG. 9A is a flow diagram that illustrates an example method for determining off-lattice 3D structure of a nucleic acid nanostructure, according to an embodiment, as described above. Although steps are depicted in FIG. 9, and in subsequent flowchart FIG. 10, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 901, a mechanical model is determined for a helix type of one or more types (also called motifs), such as a single strand helix, a continuous, nicked or gapped A-form double helix (duplex), B-form duplex, or Z-form duplex plus any version of RNA and any chemically modified or conjugated bases or nucleotides including chemical dyes and other small molecules that associate with or intercalate within the helix, proteins that are bound covalently or non-covalently to the helix, or other chemical modifications. The mechanical model includes a ground-state geometry for the location and orientations of nucleotide bases or base pairs, as well as values for one or more stiffness coefficient parameters, such as a set of six parameters for 3 translational and 3 rotational DOF. In various embodiments, the values may be functions of number of bases in helix, or base position in the helix, or base type, or may be constant. The values can be obtained from experimental measurements or simulations performed for that purpose, including sensitivity analyses, or gleaned from the literature, or inferred, or some combination. For example, ground-state geometry values for geometrical parameters for several helix types are listed in Table 1.

In step 903, a mechanical model is determined for a junction type of one or more junction types (also called motifs), such as a single strand overhang, three-way, anti-parallel stacked four-way, parallel stacked four-way, open four-way, five-way, and N-way junction types, including chemically modified junctions or junctions bound reversibly or irreversibly by secondary molecules including small organic or inorganic molecules, proteins, RNA, etc. The mechanical model includes ground-state geometry values for geometrical parameters describing the location and orientations of nucleotide bases or base pairs in or adjacent to the junction, as well as values for one or more stiffness coefficient parameters, such as a set of six parameters for 3 translational and 3 rotational DOF. The values may be functions of base location or base type or may be constant in various embodiments. The values can be obtained from experimental measurements or simulations performed for that purpose, including sensitivity analyses, or gleaned from the literature, or inferred, or some combination.

In step 911 design data is obtained that indicates the sequence of nucleotide bases in helices and strands and the locations and types of junctions. Any method may be used to specify the design data. For example, the sequence of nucleotides on a scaffold strand and the sequences of nucleotides on one or more staple strands are determined. In some embodiments, based on detailed tutorials on how to design DNA origami shapes or based on an open source DNA origami design software called caDNAno that greatly facilitates the design of a vast spectrum of DNA origami shapes available on the World Wide Web (using the hypertext transfer protocol, HTTP) at domain name cadnano for domain name extension org, a design to fabricate the nanostructure is determined during step 911. In some embodiments, the model employs a topological representation of the nucleic acid nanostructure that contains single-stranded DNA routing through duplexes and four-way junctions. In some embodiments, if sequence information is available, then sequences are saved in plain text format. These text files are read by a processor to get the sequences. If no sequence is provided, then, in some embodiments, sequences for each base are assigned to form the helices and junctions of the design while preserving the Watson-Crick base pairing.

While the program Tiamat is employed here for this purpose, the internal representation of nucleic acid strand topology is not limited to this approach. Nucleic acid strands can be joined in arbitrary geometries in 3D space, and are not required to be placed along canonical honeycomb or square lattices as previously performed by our and other groups.

In step 913, the design is interpreted as a directed graph to identify and characterize the junctions and the connecting helices in terms of types and number of bases. In some embodiments, in the directed graph, each vertex (node) is a nucleotide, and edges represent phosphate-sugar backbones and Watson-Crick base pairings. Specifically, for any given nucleotide in the nanostructure, this graph uniquely identifies the nucleotide in the 5'-direction, that in the 3'-direction, and the complementary nucleotide, if existing. The identity of each nucleotide is obtained from the sequence information in the Tiamat file. Note that the above approach is also applied to read sequence and topology from design files in caDNAno format, which places duplexes in parallel along canonical honeycomb or square lattices in contrast to the Tiamat format that allows duplexes to be placed in any position and orientation in 3D space. Junctions are indicated by adjacent nodes whose complimentary nodes (1) are not adjacent to each other and (2) are not part of a nick.

In step 915, a graph algorithm identifies all junctions together with the helix arm lengths intervening. The graph algorithm also determines the identity of each nucleotide base in each arm, and connectivity between nucleotide bases. In some embodiments, each of the connecting helixes is associated with one junction as an arm of that junction if one end of "the connecting helix" is not connected to any junction, and the other end is connected to a junction. In some embodiments, the bases of a connecting helix are divided into two contiguous sets, one associated with one junction to which it is contiguous, as an arm of that junction, and the other set associated with the other junction as an arm of that junction if both ends of "the connecting helix" are connected to junctions. Duplexes can be virtually "cut" at imaginary locations anywhere between junctions, as desired, with each subsequent daughter duplex being assigned to its closest junction thereafter. In some embodiments, the same base or base pair at the cut is included on both arms. In some embodiments, as described below, alignment element triads positioned at the ends of the subsequent daughter duplex arms are brought into register in the alignment process.

Once the directed graph is given, an algorithm is executed that automatically finds (1) junctions and (2) length of each arm in each junction. In some embodiments, sequence data was interpreted as a directed graph and junctions determined using the method depicted in FIG. 9B, described below.

In step 921, the next junction or helix in the directed graph is selected for operation. For example, each branch of the directed graph is followed from a starting node and the corresponding edge or node is selected. In step 923 the junction or helix is added to an extant structure using rest values for the geometry parameters. If the next junction or helix is the first, then there is no extant structure and the origin of a base in the junction or node is taken as the origin of the 3D coordinates. The ground-state geometry allows the next helix or junction to be added at any position in 3D coordinate space and not confined to lattice coordinates. If a finite element model is used, the junctions or helix is added as one or more finite elements of the finite element model. For example, a helix is added as a set of one or more beam elements connecting node elements corresponding to nucleotide bases or base pairs in the helix. A junction is added as a pair of alignment elements that connect each helix to a junction center, as described in more detail below.

In step 925, any misalignments are determined. For example, any connection to the extant structure that is called for by the design (e.g., the directed graph) but not possible with the ground-state geometry, is identified. The two misaligned nodes are identified with their existing positions and orientations and the information collected into a misalignment vector. If an alignment element of a finite element model is used, as described below, the alignment element is used as the misalignment vector and added to the finite element model.

In step 927, it is determined if there is another element in the design. If so, control passes back to step 921 and following steps to select the element and add it to the structure model. If not, then the initial configuration of the structure, based on rest states and misalignments, is complete; and, control passes to step 931.

In step 931, forces and moments are imposed to remove or reduce magnitudes of the misalignment vectors. A compressive or stretching force is applied along a helix or junction, or a force at a distance from a pivot (a moment) is used to bend, twist or rotate an element. In step 933, the stress is propagated throughout the structure model until a shape is achieved with which the restorative forces caused by the perturbations and stiffness coefficients balance the forces and moments applied to reduce the misalignment magnitudes. The equilibrium solution shape is computed using constraint equations that are applied to the ends of topologically connected helices to force them to become coincident and identically oriented with one another geometrically in the final configuration based on the stiffness coefficients associated with each helix and junction in the structure.

When a finite element model is used, the force balancing is done automatically. For example, the 3D mechanical ground-state solution structure is computed iteratively using the geometrically nonlinear finite element analysis using the commercial finite element software ADINA (ADINA R&D Inc., Watertown, Mass., USA), although other finite element solvers may be used in other embodiments. The simulation begins by simultaneously applying forces and moments to each pair of ends of four-way junctions that are connected by helices to obtain geometric compatibility in which the two arm ends coincide in their position and orientation in order to form a continuous helix simultaneously as the full finite element model is relaxed to adopt its mechanical equilibrium shape.

In step 935, it is determined if all misalignments are eliminated or otherwise reduced (and thus all elements are in equilibrium). If not, control passes back to steps 931 and 933 to apply and balance further forces and moments. If so, then a structural model with the position and orientation of each base, and consequently the position of each atom, is complete; and, control passes to step 941 and following steps to use the equilibrium structural model.

In step 941, the structural model of the nanostructure is presented. For example, the structure is rendered in graphical format indicating each base or each atom of each base or each atom of the entire structure including sugar backbone, absent externally applied stresses. In some embodiments, the structural model is output as data (e.g., in PDB format) for use by another software application or program, such as a graphics program.

In step 943 one or more derived properties are determined based on the structural model. For example, in various embodiments, elastic, mechanical, electromagnetic, optical, chemical or binding properties of the nanostructure are determined, alone or in some combination. In some embodiments, step 943 is performed by a separate application or program that uses the data output during step 941. For example, normal mode analysis for the equilibrium solution shape yields structural flexibility and thermal fluctuations at a given finite temperature as root-mean-square fluctuations in all DOF of all bp. In some embodiments, according to the crystallographic structure of a free four-way junction (PDB ID: 1DCW), the computational framework adjusts the coordinates of the phosphate and sugar at the crossover site in the backbone of a crossing strand in a four-way junction by rotating them by 45° about the vector from the C1' atom to the N1 atom in the same nucleotide.

In step 945, it is determined if another nanostructure design is to be processed. If so, control passes back to steps 911 and following to determine a structural model of the new design. If not, then the process ends.

Use of the finite element method enables the efficient prediction of large-scale 3D structural and mechanical properties that are not accessible to alternative computational approaches such as molecular dynamics, which is prohibitively expensive for the large-scale assemblies considered here.

In steps 913 and 915 described above, a generic programmed DNA assembly is modeled as a directed graph, which is subsequently processed in order to define the downstream finite element model. FIG. 9B is a flow diagram that illustrates an example method for determining nodes and junctions of a directed graph from sequence data for duplexes, according to an embodiment. The graph traversal algorithm includes the steps described here. A similar approach is used for strands of helices that are not duplexes. The input includes the sequence and topology information. Each node represents a nucleotide with initial Cartesian coordinates along with a unique nucleotide ID.

All DNA strands are identified in steps 951 through 957. In step 951, all nucleotides are set as "unvisited." In step 953, it is determined whether all nucleotides in the input are visited. If so, then control passes to step 971 described below. If not, then in step 957, the nucleotide sequence of the current strand is determined; and. all nucleotides in the current strand are set as "visited." The current strand is assigned a unique strand identifier (ID). Control passes back to step 953.

All multistrand junctions are identified in steps 971 through 977. In step 971, all branch points connecting two stands (e.g., DNA duplexes) are determined. Branch points are defined as graph nodes where the 3'-neighbor is contained in a different strand (e.g., duplex). In step 973, each junction is assigned a unique junction ID and a set of branch points. For example, a four-way duplex junction is assigned four branch points corresponding to the four duplex arms. In step 975, each branch point is assigned a unique branch point. In step 977, the initial position and orientation of each junction is specified. For example, if a junction is four-way duplex junction, its isomeric state is determined using the initial Cartesian coordinates of the nucleotides.

Topological connectivity between multi-way junctions and strand arm lengths are determined in steps 981 through 989. In step 981, all branch points are set as "unvisited." In step 983, it is determined whether all branch points are visited. If so, then control passes to step 989 described below. If not, then in step 985, an unvisited branch point A is found and marked as visited. A search is conducted for an unvisited branch point B that connects to A via a strand (e.g. a duplex). If found, B is set as "visited." In step 987, the lengths (number of nucleotides) of the strand arms (e.g., duplex arms) corresponding to branch point A and branch point B are determined. Control passes back to step 983.

In step 989, all nicks in duplex arms found, along with all unpaired nucleotides, are determined. The output is a set of interconnected multi-way junctions with associated connectivity and lengths of strand (e.g., duplex) arms. This output is used as describe above in step 921 and following steps.

In some embodiments, one or more steps of the method of 900 are used in an iterative process to refine the values of coefficients used in the model for one or more helix or junction types, or to refine the design of a nanostructure, or some combination. This process is described with reference to FIG. 10. FIG. 10 is a flow diagram that illustrates an example method for fabricating a nucleic acid nanostructure with controlled properties, according to an embodiment. In step 1001, the target derived properties of a nanostructure are determined, such as a target shape with one or more twists or bends, in whole or in part, or vibrational modes, or electromagnetic properties, or optical properties, or binding properties, or some combination. In some embodiments, target derived properties are not specified, and step 1001 is omitted.

In step 1003, a design to fabricate the nanostructure is determined, such as sequence of nucleotides on a nucleic acid molecule. In some embodiments, step 1003 includes obtaining a design plan file that is formatted and output by Tiamat or caDNAno.

Thus step 1003 includes determining a sequence of nucleotides on at least a first strand of a nucleic acid, or receiving data that indicates a sequence of nucleotides on at least a first strand of a nucleic acid. In some embodiments in which the nucleic acid is a double helix DNA, step 1003 also includes determining a sequence of nucleotides on each of a plurality of short strands of deoxyribonucleic acid, wherein each short strand is complimentary to a unique portion of the first strand. In some embodiments, the staple strands are complimentary to different non-contiguous segments of the scaffold strand. Thus, in some embodiments, at least one short strand is complimentary to a unique but non-contiguous segment of the first strand.

The objective of this step is to conceive a target shape that can meet certain functional requirements. For example, in light of the intended applications, one decides whether the object will be a multi-layer or a single-layer DNA origami structure or ring or hemisphere. 3D modeling software such as CHIMERA™ from University of California, San Francisco, Visual Molecular Dynamics (VMD) from University of Illinois at Urbana-Champaign, MAYA™ from AUTODESK, INC.™ of San Rafael, Calif., SKETCHUP™ from GOOGLE INC.™ of Mountain View, Calif., or TURBOCAD™ IMSI/DESIGN, LLC™, of Novato, Calif. may be of help for building and visualizing cylinder-models of the target structure. DNA origami offers the opportunity to divide the object into structural modules which can be built or changed separately. For example, a robot shaped DNA structure can be divided into three parts: a body, arms, and legs.

The design data is then retrieved, e.g., from a Tiamat or caDNAno file. For example, DNA structure design parameters include each double helix, the number of base pairs in each double helix, the location of one or more junctions.

Steps 1005 and 1007 correspond to steps 913 to 943 of method 900. In step 1005, the portions of the strands, such as the finite elements, corresponding to the design are determined, e.g., as performed during steps 913 through 927.

In step 1007 the computed derived properties of the nanostructure are determined using the physical properties of the portions, such as the finite elements, determined in step 1005 and a numerical model of mechanical interactions, such as a finite element model, as described above for steps 931 through 943. In some embodiment, the model is configured to additionally compute the normal mode shapes and associated frequencies of the nanostructure, in order to assess the mechanical stability of the structure, and to compute internal strain energies. The amplitudes of the normal mode shapes of the folded structure indicate the flexibility of the DNA structure under thermal fluctuations, and therefore whether it will be mechanically stable. The local elastic strain energy of the solution shape/deformed structure provides an indication of whether the hybridization energy will be sufficient to retain the structure in its folded form, or whether local rupture or lack of any folding whatsoever may occur. Direct calculation of derived properties due to active forcing is naturally also computed using the model, as well as alternative physical effects such as electrostatic interactions of the charged DNA backbone, steric repulsion preventing overlapping in space, and preference for dissolution in a polar medium like water (solvation energies), among others, in various embodiments. In the illustrated embodiment, computational efficiency is achieved by focusing on the first-order effects that are proposed to dominate in determining the solution shape and stability of nucleic acid nanostructures. In some embodiments, the derived property of the nanostructure is selected from a group comprising length, shape, moment of inertia for bending, moment of inertia for twisting, Young's modulus, Poisson's ratio, internal strain energy distributions, and normal modes of vibration, optical absorption and resonance. Thus, step 1007 includes determining, based at least in part on a numerical model and the physical properties for each portion, a value of at least one derived property of a nanostructure that comprises the at least first strand of nucleic acid. In these examples, the at least one derived property is selected from a group comprising relaxed shape, internal strain energy, normal modes of vibration, and stiffness, binding properties and optical properties.

In some embodiments, the model derives multiple solutions for the relaxed shape by taking different incremental steps to relax the reference forces non-linearly. For example, using different or random increments for releasing reference forces and moments, a variety of relaxed shapes are determined with corresponding internal strain energies and normal modes. The results can then be presented probabilistically, with the most common shapes given higher weight than others. Additionally, in some embodiments, each shape is inversely weighted by the internal strain energy distributions that compete with folding free energy due to base pair stacking interactions (i.e., favorable hybridization free energy).

In step 1011, it is determined whether the computed derived properties satisfy the target derived properties for the nanostructure. For example, it is determined whether the shape, moduli or eigenvalues for associated normal modes of vibration, or internal elastic strain energy distribution, binding properties or optical properties, or some combination, computed for the nanostructure are within a predetermined absolute or percent tolerance of the target values of those properties. Thus, step 1011 includes determining a difference between the value of the at least one derived property of the nanostructure and a target value of the at least one derived property. If the computed derived properties do not satisfy the target derived properties, e.g., are not within a predefined threshold, control passes to step 1013 to change one or more of the nucleotide sequences used in the design determined during step 1003.

In step 1013, one or more of the nucleotide sequences used in the current design of the nanostructure is changed. For example a nucleotide is inserted or deleted in one or more helices, e.g., to move a junction or change a junction type, to induce reduced or enhanced twist or bending, or both, to more closely resemble the target derived property. This change may be selected from a large number of alternatives using combinatorial or other optimization algorithms. The initial distribution of nucleotide sequences may also be chosen using such algorithms in order to obtain a first attempt of the desired target structure, after which the structural model is produced to calculate values of derived properties, which are then used to inform/update the scaffold/stable design iteratively. Thus, step 1013 includes determining a change in the sequence of nucleotides based on the difference. Control then passes back to step 1003 for determining the new sequences or to step 1005 for determining the new corresponding finite elements, and to step 1007 to compute the new derived properties of the nanostructure.

By repeated operation of the loop formed by steps 1003 or 1005, 1007, 1011 and 1013, the computed derived properties are made to converge arbitrarily close to the target derived properties desired for the nanostructure. Following this loop provides the advantage of preventing the wasteful expenditure of resources, including time and money. The software gives the 3D structure, which can be compared with the target structure to see if it looks correct. For example, the computational loop prevents wasting resources making the dozens or hundreds of staple strands for scaffolded DNA origami only to find that the resulting structure always folds or includes appendages that constantly flop out of alignment in response to external vibrations or Brownian motion. Experimental yield of the folded target structure may also be maximized by minimizing internal strain energy distributions that compete with folding free energy due to base pair stacking interactions (i.e., favorable hybridization free energy). Thus a repeat of step 1005 and 1007 includes determining, based at least in part on the numerical model and the physical properties for each portion, a revised value of at least one derived property of a revised nanostructure that comprises the change in the sequence of nucleotides. And a repeat of step 1011 includes determining a revised difference between the value of the at least one derived property of the nanostructure and the target value.

When the computed derived properties satisfy the target derived properties, then control passes to step 1021 to begin fabrication of the nanostructure. If no target properties are specified in step 1001, or if step 1001 is omitted, then all computed values are found to satisfy the target and control passes directly from step 1007 to step 1021.

In step 1021 the constituent strands are prepared according to the final sequences that satisfy the target derived properties, if any, including any fabrication or assembly of such component strands. For example, in scaffolded DNA origami, depending on the size of the scaffold template strand, a single DNA origami shape may require a few hundred unique staple strands (e.g., oligonucleotide sequences). The in-house laboratory synthesis of these many different staple oligonucleotides is often not practical unless multiple DNA synthesizers running in parallel are available. High-throughput chemical synthesis of oligonucleotides on well plates including purification steps such as reverse-phase cartridge purification that largely remove truncated synthesis products is offered by a range of commercial vendors such as EUROFINS MWG OPERON™ of Huntsville, Ala., BIONEER, INC.™ of Alameda Calif., and ILLUMINA, INC.™ of San Diego, Calif. When ordering plate oligonucleotide synthesis one should consider ordering concentration-normalized oligos such that each staple oligonucleotide in each well is dissolved to the same concentration, for example 100 microMolar ($\mu M$, 1 $\mu M=10^{-6}$ Molar) concentration in either distilled water or in buffer. For convenience during later pipetting, it is advisable to group the staple oligonucleotides on the well plates according to the structural module to which they belong. For building an example robot-shaped structure, three 96-well plates were ordered. All the staple oligonucleotides that form the body of the structure are located on plate 1 and partially on plate 2, while the staples for building the limbs are found on plates 2 and 3.

A number of custom-length variants of the M13mp18 single-stranded bacteriophage genome have been tested and work robustly as templates for scaffolded DNA origami. Beyond the wild-type 7249 bases-long M13mp18 genome, variants of length 7308, 7560, 7704, 8064, and 8634 bases, respectively, have been cloned, and arbitrary sub-fragments of single-stranded DNA scaffold can be generated using restriction enzymes in a straightforward manner. An easy but cost-intensive way to prepare single-stranded scaffold DNA is to simply purchase M13 single-stranded bacteriophage genome from vendors such as NEW ENGLAND BIO-LABS™ of Ipswich, Mass., or BAYOU BIOLABS™ of Metairie, La. Purely synthetic single-stranded DNA can alternatively be purchased from other commercial providers. In principle any scaffold can be used from any virus or other source of single-stranded DNA, including restriction enzyme cut and ligated ssDNA, and asymmetric PCR can also be used to amplify specific segments of single-stranded DNA. Single-stranded templates may also be prepared by enzymatic digestion of one strand in double-stranded plasmid DNA. Custom single-stranded templates also have been produced by magnetic-bead separation of polymerase-chain-reaction amplicons as described elsewhere. Double-stranded templates that are separated during the assembly process itself have also been successfully used for building DNA origami shapes. However, folding complex shapes from double-stranded templates may prove more challenging than folding these shapes from single-stranded templates. Once scaffold DNA has been purified or purchased, it should be aliquoted and stored at −20 degrees Celsius at a convenient standard concentration of for example 100 nanoMolar (nM, 1 nM=$10^{-9}$ Molar). An example robot shaped structure was folded from a previously reported 8064-bases-long variant cloned from the M13mp18 bacteriophage genome which was stored frozen at 100 nM concentration in 10 milliMolar (mM, 1 mM=$10^{-3}$ Molar) TRIS-Base and 1mM EDTA at pH 8. Complementary synthetic strands that Watson-Crick base-pair with the scaffold strand are chosen based on existing criteria in the design of scaffolded DNA origami objects (e.g., see Castro et al., "A primer to scaffolded DNA origami", *Nature Methods*, v8, #3, pp 221-229, 2011, Pan et al., "Lattice free prediction of three-dimensional structure of programmed DNA assemblies," *Nature Communications*, 5:5578 doi: 10.1038/ncomms6578, 2014, the entire contents of each of which is hereby incorporated by reference as if fully set forth herein). Synthetic staple strands are purchased from INTEGRATED DNA TECHNOLOGIES, INC.™ of Coralville, Iowa, or other commercial provider. One-pot reactions are used to self-assemble DNA origami objects in standard manner using a time-based thermal annealing protocol in standard buffers as previously published (see Castro 2011 and Pan 2014, cited above)

In step 1023, one or more nanostructures are prepared based on the final constituent strands, such as the final scaffold strand and final staple strands for scaffold DNA origami, as prepared in step 1021. Step 1023 is a chemical self-assembly, called hybridization. Thus, step 1023 includes preparing the nanostructure based at least in part on the design data. If step 1013 is performed, then step 1023 includes fabricating the nanostructure based on the change in the sequence of nucleotides on at least the design data, if the revised difference does not exceed the predetermined threshold.

In step 1025, the nanostructures prepared during step 1023 are utilized. For example the nanostructures are introduced into a biological system for diagnosis or treatment of conditions, or attached to a substrate for testing samples or providing functionalized surface of electronic or microelectromechanical systems (MEMS). In an illustrated embodiment, step 1025 includes examining the nanostructures to determine the actual shape or stiffness or internal elastic strain energy distributions or vibrational modes of the nanostructure. Thus, in some embodiments, step 1025 includes determining a measured value of the at least one derived property of the prepared nanostructure based on a measurement of the prepared nanostructure.

For example, extended DNA origami structures are imaged three-dimensionally using either negative-stain or cryogenic transmission electron microscopy (TEM) in various embodiments, while flat objects are conveniently imaged with atomic force microscopy (AFM). Shape heterogeneity is assessed on a particle-by-particle basis, in some embodiments. Image processing is used, in some embodiments, to identify systematic structural flaws or to reconstruct three-dimensional models from single-particle TEM data. Cryo-TEM has been used to reconstruct a 3D model of a single-layer fold-up box, while negative-stain TEM with 2% uranyl formate as staining agent has proved to be a convenient tool for imaging stiffer multi-layer DNA origami objects.

In some embodiments, step 1025 includes mechanical testing of structure elastic properties or vibrational normal modes optical properties or internal strain energy distributions. Thus step 1025 includes determining a measured value of at least one derived property of the fabricated nanostructure based on a measurement of the fabricated nanostructure.

If a shape does not meet the set structural specifications, the workflow is restarted at step 1013, where other internal scaffold/staple lay-out arrangements are worked out, or from step 1023 where different hybridization conditions are tested. Pooling the staple molecules by structural modules facilitates exchanging staples for a particular part of the object that may need redesigning. In case of a satisfying result of the structural analysis, one moves to further processing or direct application in step 1025, in various embodiments. Further processing may consist of assembling of multiple DNA origami objects into higher-order multimers (aggregates) or it may involve, for example, large-scale purification and concentrating the shapes to liquid crystalline conditions. In one such embodiment, purification produced DNA origami nanotubes that have found use as an alignment media for the structural analysis of membrane proteins by nuclear magnetic resonance.

In step 1031, it is determined whether the values of the parameters describing the geometric and physical properties or portions of strands, such as finite elements, should be refined. In some embodiments, the finite elements and the associated values for ground-state geometry and stiffness coefficients are fixed and step 1031 is omitted. If finite elements are not to be refined, or if step 1031 is omitted, then in step 1033 it is determined if end conditions are satisfied, such as closing a computer program implementing the method 1000. If so, the process ends. Otherwise the process continues at step 1001.

In some embodiments, physical properties or finite elements are to be refined. In these embodiments, control passes from step 1031 to step 1035. In step 1035, systematic differences between computed and measured derived properties are taken as an indication that the finite elements or associated values are in error and should be revised, at least slightly. For example, values of physical properties of stiffness coefficients are revised. In some embodiments, undetectable systematic differences between computed and measured derived properties are taken as an indication that the finite elements are smaller than needed to resolve the properties of interest and should be combined into larger elements, such as beams of 7 base pair length, or single beams between junctions, or fewer junction types, for faster computations. Control then passes to step 1033, described above.

Using the above methods, initial positions of each base are determined by connecting helices to junctions using the rest geometry and arbitrary coordinates not confined to lattice coordinates or lattices in which double-helices are parallel or anti-parallel at junctions. Closed topological structures can also be treated, unlike previous approaches.

2. Example Embodiments

The methods 900 and 1000 have been applied to a wide variety of DNA nanostructures using double helices, as described in this section.

2.1 Alignment Elements

In some embodiments, the misalignment vector (e.g., vectors 634 and 635) are described using alignment elements of a finite element model, e.g., the alignment elements available in a commercial finite element analysis program ADINA Version 9.0 from ADINA R&D Inc., Watertown, Mass. Each alignment element is used to characterize any misalignment between two nodes of the finite element model, such as the terminal nucleotide bases or base pairs on two arms that should be connected, or nucleotide bases or base pairs on the two arms connected at a junction which are closest to the center of the junction or span the crossover.

FIG. 6B is a block diagrams that illustrates an example alignment element of a finite element model, used to characterize misalignments in non-final configurations, according to an embodiment. The two nodes that are to be aligned are indicated by node $n_1$ with spatial coordinates $a_{10}$ 650, and node $n_2$ with coordinates $a_{20}$ 660. Each node is represented by a pair of triads, an A triad and a B triad, that each indicate an origin and orientation. The A triad is centered on the node and gives its orientation frame, the B triad of the pair is centered on the location and orientation of some point (e.g., a starting point, midpoint, or an ending point) between the current node and the next node. Initially, the B triad is placed and oriented based on the ground-state geometry for the helix or junction. The difference between the B triads of the two nodes is the misalignment vector for these embodiments. It is removed or reduced by applying forces and moments that deform the geometry of the other components of the structure, e.g., incrementally in a finite element model.

For example, as depicted in FIG. 6B, the A triad of node $n_1$ has origin $a_{10}$ 650 and reference frame axes $a_{11}$ 651, $a_{12}$ 652 and $a_{13}$ 653. The B triad of node $n_1$ has origin $b_{10}$ 656 and reference frame axes $b_{11}$ 657, $b_{12}$ 658 and $b_{13}$ 659 expressed in the global 3D coordinate system. The same items relative to the A triad reference frame are indicated by the hatted symbols, $\hat{b}_{10}$, $\hat{b}_{11}$, $\hat{b}_{12}$, $\hat{b}_{13}$, respectively. The two triads are connected by rigid element 654 which indicates the rest changes in position from the first node $n_1$ to the point toward the second node $n_2$, e.g., the midpoint. Thus, represented in the global reference frame, the B triad of node $n_1$ has the center $b_{10}=a_{10}+(a_{11}, a_{12}, a_{13})\hat{b}_{10}$, where $(a_{11}, a_{12}, a_{13})$ is a matrix with $a_{11}, a_{12}, a_{13}$ as three columns, and three axes $b_{11}, b_{12},$ and $b_{13}$ given by $(b_{11}, b_{12}, b_{13})=(a_{11}, a_{12}, a_{13})(\hat{b}_{11}, \hat{b}_{12}, \hat{b}_{13})$.

Similarly, the A triad of node $n_2$ has origin $a_{20}$ 660 and reference frame axes $a_{21}$ 661, $a_{22}$ 662 and $a_{23}$ 663. The B triad of node $n_2$ has origin $b_{20}$ 666 and reference frame axes $b_{21}$ 667, $b_{22}$ 668 and $b_{23}$ 669 expressed in the global 3D coordinate system. The same items relative to the A triad reference frame are indicate by the hatted symbols, $\hat{b}_{20}$, $\hat{b}_{21}$, $\hat{b}_{22}$, $\hat{b}_{23}$, respectively. The two triads are connected by rigid element 664 which indicates the rest changes in position from the second node $n_2$ to midpoint toward first node $n_1$. Thus, represented in the global reference frame, the B triad of node $n_2$ has the center $b_{20}=a_{20}+(a_{21}, a_{22}, a_{23})\hat{b}_{20}$ and axes $(b_{21}, b_{22}, b_{23})=(a_{21}, a_{22}, a_{23})(\hat{b}_{21}, \hat{b}_{22}, \hat{b}_{23})$.

The difference in positions and orientations of the two B triads gives the misalignment vector 670. The misalignments between B triads of nodes $n_1$ and $n_2$ are calculated in three translational DOF along the three axes $b_{11}, b_{12},$ and $b_{13}$ of the B triad of node $n_1$ and in three rotational DOF about axes $b_{11}, b_{12},$ and $b_{13}$. The translational misalignments, t, along axes $b_{11}, b_{12},$ and $b_{13}$ are given by Equation 1a through 1c.

$$t_1=(b_{20}-b_{10})\cdot b_{11} \tag{1a}$$

$$t_2=(b_{20}-b_{10})\cdot b_{12} \tag{1b}$$

$$t_3=(b_{20}-b_{10})\cdot b_{13}, \tag{1c}$$

respectively. The rotational misalignments about axes $b_{11}, b_{12},$ and $b_{13}$ are calculated from the rotation matrix R from the B triad of node $n_1$ to that of node $n_2$ given by Equation 2.

$$R = \begin{pmatrix} b_{11}\cdot b_{21} & b_{11}\cdot b_{22} & b_{11}\cdot b_{23} \\ b_{12}\cdot b_{21} & b_{12}\cdot b_{22} & b_{12}\cdot b_{23} \\ b_{13}\cdot b_{21} & b_{13}\cdot b_{22} & b_{13}\cdot b_{23} \end{pmatrix} \tag{2}$$

which can be represented using a rotation axis $(x_1, x_2, x_3)^T$ and a rotation angle $\theta_{1\rightarrow 2}$. The rotational misalignments, r, about axes $b_{11}, b_{12},$ and $b_{13}$ are then given by Equations 3a through 3c.

$$r_1=\theta_{1\rightarrow 2}x_1 \tag{3a}$$

$$r_2=\theta_{1\rightarrow 2}x_2 \tag{3b}$$

$$r_3=\theta_{1\rightarrow 2}x_3. \tag{3c}$$

The alignment element is used in the finite element model to calculate the alignment forces and moments to remove the misalignment. The translational stiffness coefficients are denoted by $k_{t1}, k_{t2},$ and $k_{t3}$, and the rotational stiffness coefficients are denoted by $k_{r1}, k_{r2},$ and $k_{r3}$. The alignment forces $F_1, F_2,$ and $F_3$ and moments $M_1, M_2,$ and $M_3$ are given by Equations 4a through 4c and 5a through 5c, respectively.

$$F_1=k_{t1}(b_{20}-b_{10})\cdot b_{11}=k_{t1}t_1 \tag{4a}$$

$$F_2=k_{t2}(b_{20}-b_{10})\cdot b_{12}=k_{t2}t_2 \tag{4b}$$

$$F_3 = k_{t3}(b_{20}-b_{10}) \cdot b_{13} = k_{t3}t_3 \quad (4c)$$

$$M_1 = k_{r1}\theta_{1 \to 2}x_1 = k_{r1}r_1 \quad (5a)$$

$$M_2 = k_{r2}\theta_{1 \to 2}x_2 = k_{r2}r_2 \quad (5b)$$

$$M_3 = k_{r3}\theta_{1 \to 2}x_3 = k_{r3}r_3 \quad (5c)$$

2.2 Alignment of Arms of Junctions

To compute the three-dimensional solution shape of nucleic acid nanostructures, in some embodiments, individual junctions are connected using the alignment element described above. An alignment element displaces the two nodes at the A triads located at the ends of two helices in order for their B triads denoted by $n_b$ and $n_t$, to overlap with each other without any translational and rotational mismatch. Here first subscripts b and t corresponds to first subscripts 1 and 2, respectively, in FIG. 6B. When used for junctions, the B triads are at the rest geometrical position of the center of the junction connected to the base or base pair; and a misalignment between the rest geometries of the junction centers from the joined helices is allowed, based on the stiffness of the junction. When used to connect the same base or base pair at the end of two different arms, the B triads are centered on the A triads and no misalignment between the B triads is allowed.

Figure 8A:
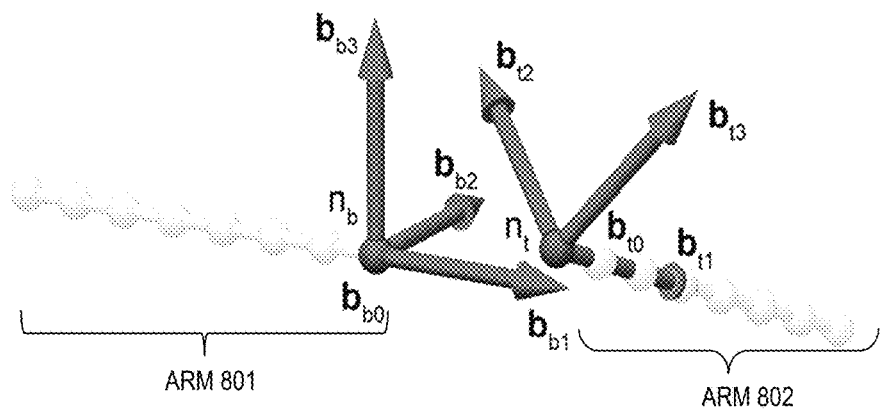
FIG. 8A through FIG. 8D are block diagrams that illustrate example use of alignment elements to determine deviations from ground-state geometry at ends of helix arms of a junction, according to an embodiment.
Figure 8B:
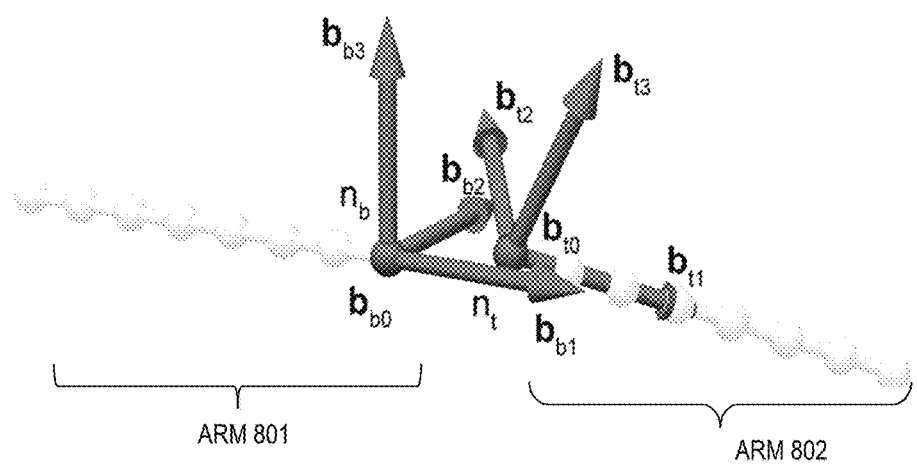
Figure 8C:
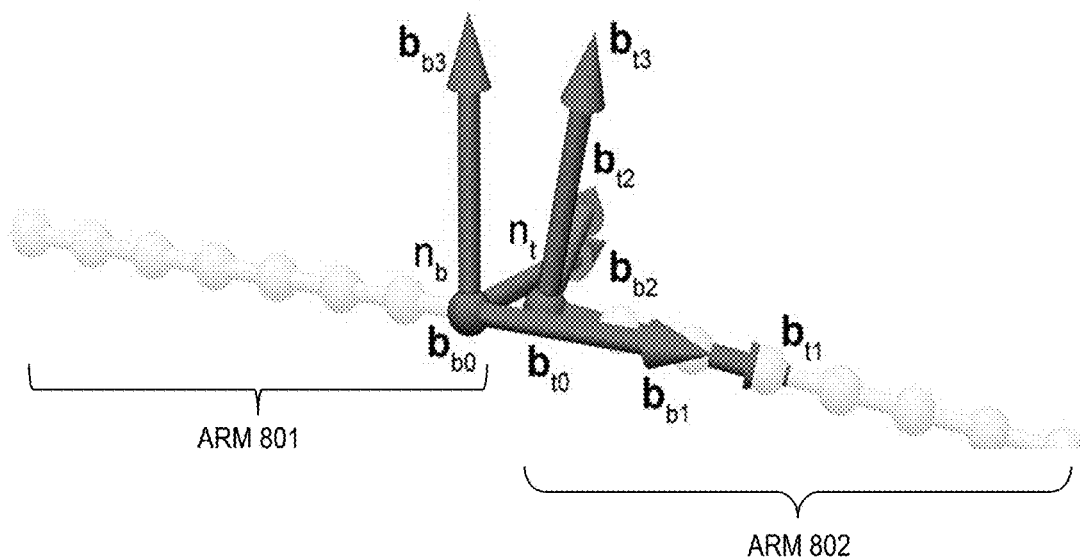
Figure 8D:
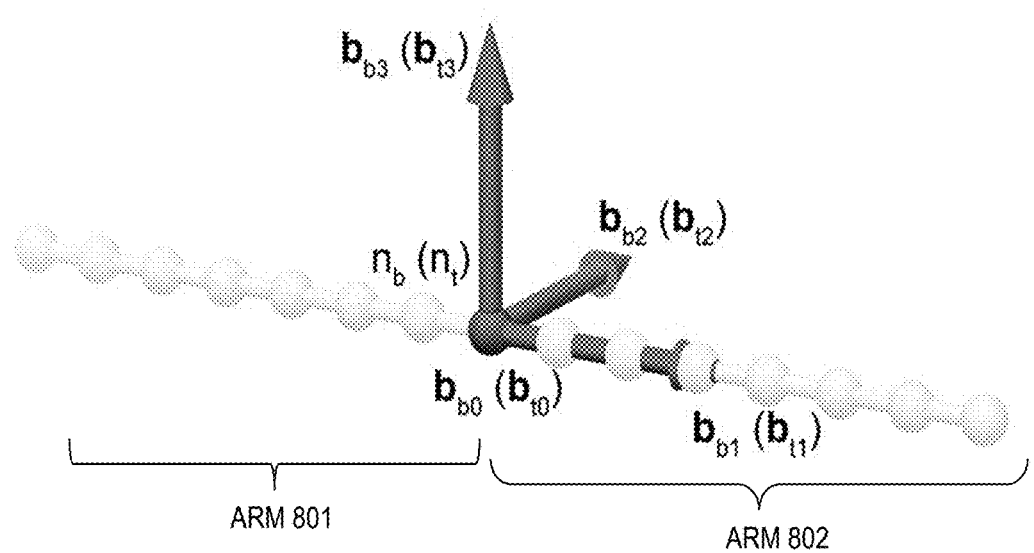

FIG. 8A through FIG. 8D are block diagrams that illustrate example use of alignment elements to eliminate misalignments at ends of helix arms 801 and 802 of two junctions, according to an embodiment. Nodes and beam elements corresponding to each base or base pair in each helix arm are rendered as spheres and cylinders, respectively. Nodes at two termini are labeled $n_b$ and $n_t$; and in this embodiment indicate the same base or base pair. Thus nodes $n_b$ and $n_t$ must have the same position and orientation after alignment. Thus, the B triads have the same position and orientation as the A triads and the final alignment must have a misalignment magnitude of zero in every degree of freedom. The centers and axes of the two B triads rigidly attached to the two nodes are marked. As shown in FIG. 8A, two B triads are rigidly attached to $n_b$ and $n_t$, respectively, whose centers are $b_{b0}$ and $b_{t0}$. Axes $b_{b1}$ and $b_{t1}$ are along the helix axes, and the other axes are determined using the ground-state geometry of the helix (e.g., 10.5 by per turn for a B-form DNA duplex). The forces and moments applied to $n_b$ and $n_t$ required for alignment are calculated using equations 4a through 5c. For B-form duplex connected at a stacked four-way junction, the stiffness coefficients are chosen to be $k_{t1} = k_{t2} = k_{t3} = 10^3(S_{dsDNA}/L) = 3.24 \times 10^6$ pN/nm, $k_{r1} = k_{r2} = 10^3(B_{dsDNA}/L) = 6.76 \times 10^5$ pN nm/rad, and $k_{r3} = 10^3(T_{dsDNA}/L) = 1.35 \times 10^6$ pN nm/rad. Time evolution of the finite element model is depicted in FIG. 8A through FIG. 8D.

2.3 Alignment of Antiparallel, Stacked Four-way Junction

Stacked-X immobile four-way junctions are core structural motifs of programmed DNA assemblies. A stacked-X four-way junction consists of two sets of coaxially stacked duplex arms as two continuous helices. An arbitrarily chosen helix is defined as the bottom helix (BH), and the other helix is defined as the top helix (TH). The termini of arms 1 and 3 of the four-way junction are defined as the 5'-end of the non-crossing strands in the BH and TH, respectively. Similarly, the termini of arms 2 and 4 are the 3'-end of the non-crossing strands in the BH and TH, respectively.

Figure 7A:
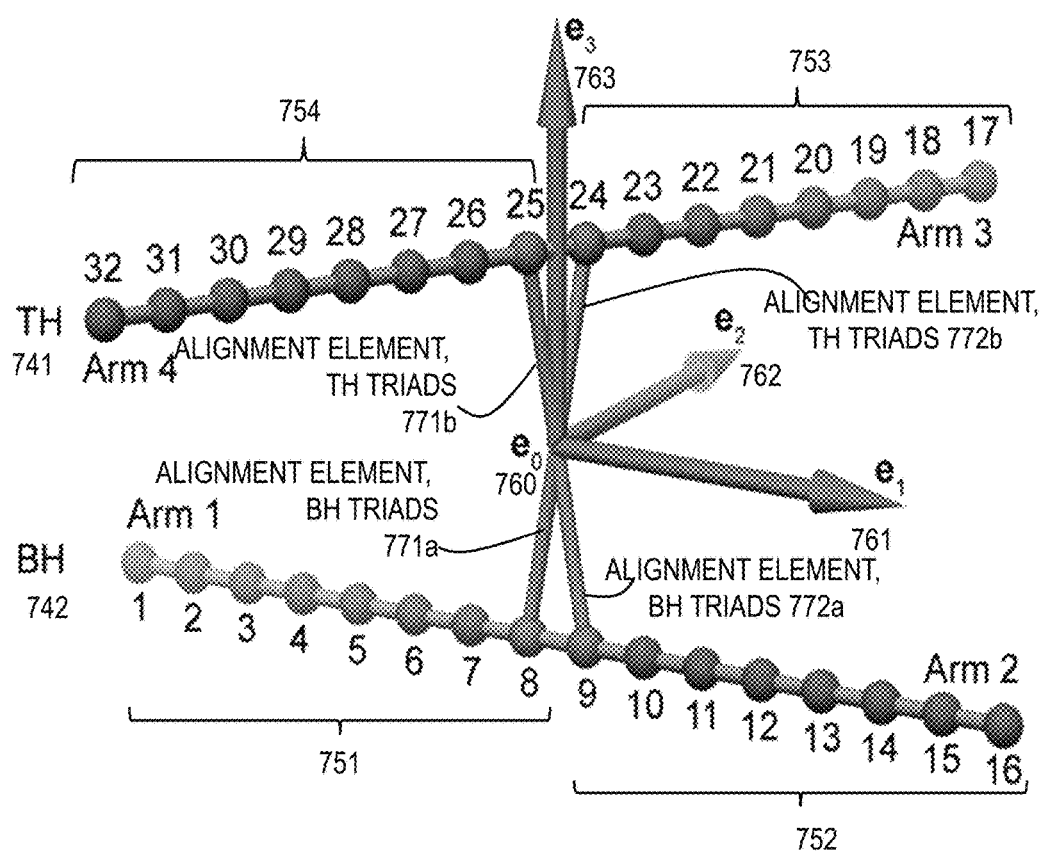
FIG. 7A and FIG. 7B are block diagrams that illustrate example use of alignment elements to determine deviations from ground-state geometry in a junction, according to an embodiment.
Figure 7B:
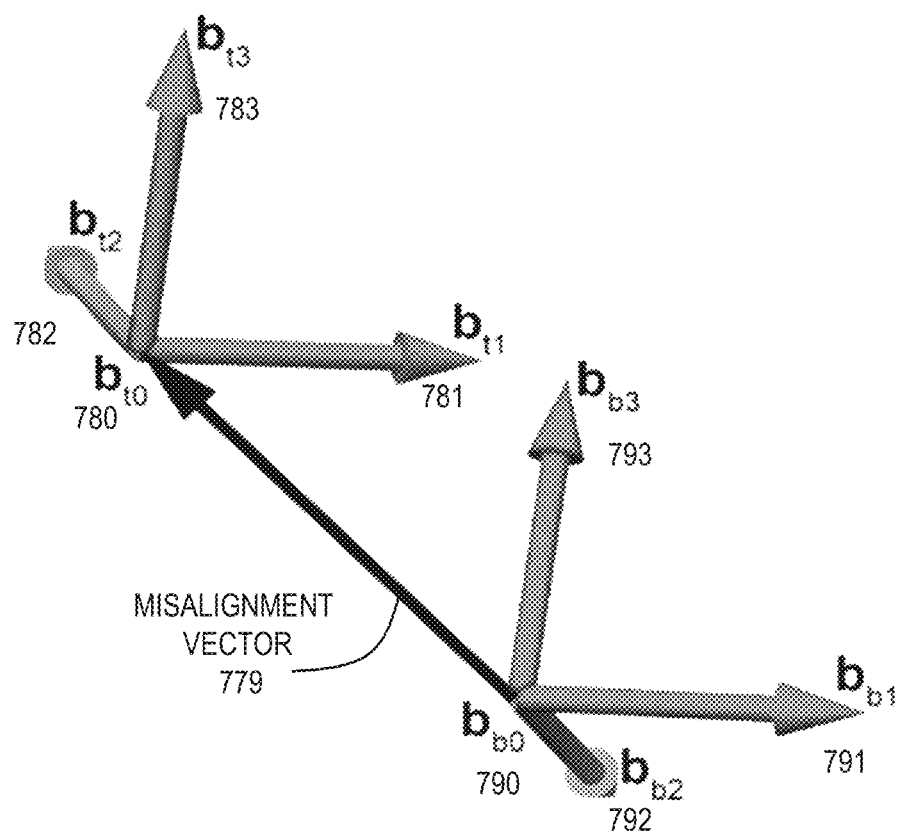

FIG. 7A and FIG. 7B are block diagrams that illustrate example use of alignment elements to determine deviations from ground-state geometry in a junction, according to an embodiment. For purposes of illustration, it is assumed that a finite element model is being built of a stacked-X four-way junction with 32 base pairs (bps) at its rest state, or the state with zero mechanical stress (also called a ground state), described in FIG. 7A. The 16-bp-long BH 742 and TH 741 are modeled as two beams with stretch modulus $S_{dsDNA}=1100$ pN, bend modulus $B_{dsDNA}=230$ pN nm$^2$, and twist modulus $T_{dsDNA}=460$ pN nm$^2$. Each by is modeled as a finite element node labeled 1 through 32 as shown in FIG. 7A. A junction reference frame defined by its center position $e_0$ 760 and three directional vectors $e_1$ 761, $e_2$ 762 and $e_3$ 763 together with two geometric parameters, inter-helical distance s and inter-helical angle $J_{twist}$, uniquely determines the initial shape of the ground-state finite element model for the junction, as described above with reference to FIG. 5E and FIG. 5F. The definition of the junction reference frame was derived above with reference to FIG. 5A through FIG. 5D. Base pairs 1 through 8 form arm 1 751, base pairs 9 through 16 form arm 2 752, base pairs 17 through 24 form arm 3 753, and base pairs 25 through 32 form arm 4 754.

At the ground state, both BH 742 and TH 741 are straight, and the position and orientation of each node can be calculated from s and $J_{twist}$. For example, the center of the BH, or the midpoint of nodes 8 and 9 at the crossover site in FIG. S1A, has coordinate (0, 0, −s/2) in the reference frame. Similarly, the midpoint of nodes 24 and 25 at the crossover site in the TH has coordinate (0, 0, s/2) in the reference frame. The spatial vector in the BH from the terminus of arm 1 (node 1) to that of arm 2 (node 16) is collinear with $e_1$ while the vector in the TH from the terminus of arm 4 (node 32) to that of arm 3 (node 17) is collinear with a unit vector obtained by rotating $e_1$ by $J_{twist}$ about $e_3$. The finite element nodes are then placed on the BH and TH using the axial rise per by (L=0.34 nm) and the right-handed twisting angle per by (360°/10.5) about the helical axis of the B-form DNA.

BH and TH are connected at the junction site using two individual alignment elements that define the flexibility of the junction. One alignment element 771 connects nodes 8 and 25 to the junction center using triad pairs 771a and 771b, respectively; while the other alignment element 772 connects nodes 9 and 24 to the junction center independently, using triad pairs 772a and 772b, respectively. The two B triads of each alignment element are defined to be the expected center of the junction in the rest state. For each alignment element, a B triad with its center position $b_{b0}$ and three directional vectors $b_{b1}$, $b_{b2}$, and $b_{b3}$ is rigidly attached to the node in the BH, e.g. node 8 or 9, and similarly another B triad with its center position $b_{t0}$ and three directional vectors $b_{t1}$, $b_{t2}$, and $b_{t3}$ is rigidly attached to the node in the TH, e.g. node 25 or 24, respectively. Again, the first subscripts b and t correspond to the first subscripts 1 and 2, respectively, in FIG. 6B. For each of the two alignment elements, the two B triads overlap with the reference frame at the ground state, i.e., $b_{bi}=b_{ti}=e_i$, i=0, 1, 2, & 3.

FIG. 7B illustrates misalignments from the two B triads rigidly attached to the A triads for base pairs in the BH and TH. All the base pair nodes and beam elements are omitted for clarity. These misalignments are reduced by forces and moments that balance restorative forces and moments in the alignment element, which are given by Equations 4a through 5c.

Thus, a finite element model for a stacked-X four-way junction is constructed using the geometric parameters s and $J_{twist}$ and the mechanical parameters $k_{t1}$, $k_{t2}$, $k_{t3}$, $k_{r1}$, $k_{r2}$, and $k_{r3}$, assumed to be constant Here, the junction is assumed to be rigid in three translational DOF, $k_{t1}=k_{t2}=k_{t3}=2\times10^3(S_{dsDNA}/L)6.47\times10^6$ pN/nm (Table 1). The remaining five parameters, s, $J_{twist}$, $k_{r1}$, $k_{r2}$, and $k_{r3}$, were determined for this type junction as described in the following sections 2.4 Geometric Parameter Values for Stacked Four-way Junction As illustrated in FIG. 5E and FIG. 5F, the geometry for this junction type depends on the inter-helical distance s and the inter-helical angle $J_{twist}$. Low temperature electron microscopy (also called electron cryomicroscopy, or Cryo-EM) revealed structure of a megadalton-scale DNA origami nanostructure and suggests an inter-helical distance of s=about 1.85 nm.

There have been various experimental and computational approaches to determine the ground-state inter-helical angle $J_{twist}$ between two sets of coaxially stacked duplex arms in a stacked-X four-way junction. For example, Förster Resonance Energy Transfer (FRET) has been used to obtain the angle by measuring the distance between chromophores attached to the termini of the four-way junction arms. Time-resolved FRET further yielded the probability distribution of the angle. Birefringence decay time was also measured from which the angle can be calculated. Molecular modeling procedures are used, in some embodiments, to generate molecular models of four-way junctions and minimize their internal energy to compute this angle $J_{twist}$ may also be obtained using the crystal packing model of B-form DNA.

In addition, atomic force microscopy (AFM) images of synthesized DNA parallelograms consisting of a lattice of four-way junctions enable direct measurement of the inter-helical angle. For AFM imaging, 1 mL sample was deposited onto a slide of freshly pealed mica (Ted Pella, Inc.) and left for 0.5 minutes for adsorption. 80 mL 1×TAE-$Mg^{2+}$ buffer was added on top of the sample and an extra 40 mL of the same buffer was added on the window of the AFM tip. The sample was scanned in the scan-analysis in fluid mode using AFM (Dimension FastScan, Bruker Corporation) with SCANASYST-FLUID+ tips (Bruker, Inc.). All of these preceding approaches have reported a consensus value of approximately 60° for the angle.

On the other hand, atomistic structures determined by X-ray crystallography yield smaller inter-helical angles of approximately 40°, which does not result from crystal packing. AFM has shown that the angle can take on different values in the range of about 40° to about 60° depending on the local sequences flanking the junctions. This sequence dependence of four-way junction structure has also been observed in crystallographic studies. Based on these previous studies, we adopt the inter-helical distance of s=1.85 nm and the inter-helical angle of $J_{twist}$=60° in the present work, as summarized in Table 2. Other embodiments incorporate the sequence-dependence of $J_{twist}$.

2.5 Stiffness Parameter Values for Stacked Four-way Junction

To estimate the rotational stiffness coefficients $k_{r1}$, $k_{r2}$, and $k_{r3}$ for the junction, molecular dynamics (MD) simulations were performed to sample the conformational space of unconstrained four-way junctions, and then the corresponding stiffness coefficients were estimated using the Equipartition Theorem of statistical mechanics. The estimated stiffness coefficients were also validated using previous experimental FRET measurements of a four-way junction, summarized in Table 2.

MD simulations depend on the distribution of atoms in the molecule. The nucleotide positions and orientation are used to deduce the atomic structure of the nanostructure using the convention of 3DNA frames, depicted in FIG. 5A.

For example, the atomistic structure of a four-way junction consisting of four 10-mer chains (PDB ID: 1DCW) were considered. First, as shown in FIG. 5B, four reference base pairs (bp) frames (Frame 1 to Frame 4) are created on the four bps flanking the crossover sites of the junction using the convention of the software 3DNA. Frame 1 is located on the by defined by residue 8 in chain B and residue 3 in chain C, hereafter denoted as (B.8, C.3). In FIG. 5A, $e_{i0}$, $e_{i1}$, $e_{i2}$, and $e_{i3}$ represent the by center, a unit vector perpendicular to the by plane, a unit vector pointing to the minor groove, and a unit vector pointing to the first base of frame i, respectively. Then, the center ($e_{b0}$) and three directional vectors ($e_{b1}$, $e_{b2}$, $e_{b3}$) of frame BH is calculated by averaging those of frames 1 and 2 while the center ($e_{t0}$) and three directional vectors ($e_{t1}$, $e_{t2}$, $e_{t3}$) of frame TH is determined from frames 3 and 4 as shown in FIG. 5C and FIG. 5D.

Using frame BH as the reference, the rotation matrix from frame BH to frame TH is given by Equation 2, where the first subscripts 1 and 2 correspond to first subscripts b and t, respectively. The rotation can be represented using a rotation axis $(x_1, x_2, x_3)^T$ and a rotation angle $\theta_{1 \to 2}$. The rotational misalignments, $r_1$, $r_2$, $r_3$, about axes $b_{b1}$, $b_{b1}$, and $b_{b3}$, respectively, between BH and TH are then given by Equations 3a through 3c, where 1 is replaced by b in the first subscript.

According to the Equipartition theorem, the mean potential energy of each rotational degree of freedom equals $k_B T/2$, where $k_B$ is the Boltzmann constant and T is the temperature of the system. Hence the rotational stiffness coefficients for the junction can be obtained from Equations 6a through 6c.

$$k_{r1} = k_B T / \text{var}(r_1) \quad (6a)$$

$$k_{r2} = k_B T / \text{var}(r_2) \quad (6a)$$

$$k_{r2} = k_B T / \text{var}(r_3) \quad (6a)$$

where var( ) denotes the variance of the parameter enclosed in parenthesis.

Four independent 100-ns-long MD simulation replicates were performed using the crystal structure of the four-way junction PDB ID 1DCW9. Explicit Mg2+, Na+, and Cl-ions were fitted to the DNA electrostatic potential in the absence of water using the CIonize to produce a zero net charge and salt concentrations of 18 mM MgCl2 and 5 mM NaCl, consistent with experimental conditions; followed by immersion in a periodic cubic box of explicit TIP3P water. Simulations were performed in the isothermal-isobaric ensemble at 300K and 1 atm using the software NAMD and the CHARMM parameter set with modified Mg2+ parameters. Temperature and pressure were maintained using the Langevin dynamics and Langevin piston formalisms according to the protocol used for explicit simulation of 1DCW32. A 2 fs time-step was used with all hydrogens constrained to their equilibrium lengths using the SHAKE and RATTLE algorithms. A shifted cut-off from 10 to 12 Å was used, with long-range electrostatics represented by Particle Mesh Ewald summation. 5,000 steps of energy minimization were performed with the conjugate-gradient line minimizer, followed by controlled heating and equilibration over 6 ns before final production runs of 100 ns each. The same force field, ion and solvent models were used for the minimization, equilibration, and final production runs.

Junction conformations were stored every picosecond from 20 ns to 100 ns in each MD simulation. Thus, 320,000 conformations were sampled in total from the four MD simulations. For each sampled conformation, the three angles $r_1$, $r_2$, $r_3$ were computed using Equations 3a through 3c. The calculated variances were var $(r_1)$=0.023 rad$^2$, var($r_2$)=0.032 rad$^2$, and var($r_3$)=0.027 rad$^2$ resulting in $k_{r1}$=181 pN nm/rad, $k_{r2}$=128 pN nm/rad, and $k_{r3}$=151 pN nm/rad, respectively.

Note that the MD simulations only sample conformations with inter-helical angle $J_{twist}$ close to its ground-state value. The MD calculations are only used to fix the value of stiffness coefficient $k_{r3}$ in some circumstances. The values of two stiffness coefficients, $k_{r1}$ and $k_{r2}$, are not chosen exactly following the MD calculations; instead, they are chosen based upon the bend modulus of double-stranded DNA. Thus, the stiffness coefficients were chosen as $k_{r1}$=$k_{r2}$=2 (B$_{dsDNA}$/L)=1,353 pN nm/rad. The MD results were adopted for the third stiffness coefficient that was set as $k_{r3}$=0.1 (T$_{dsDNA}$/L)=135.3 pN nm/rad if all four-way junctions in the structure have the inter-helical angles in the vicinity of the natural 60° angle for the junctions. Otherwise $k_{r3}$ was reduce by an order of magnitude and set $k_{r3}$=0.01(T dsDNA/L)= 13.53 pN nm/rad f. Table 2 lists all the stiffness coefficients of the four-way junction model.

The rotational stiffness coefficient $k_{r3}$ corresponding to the inter-helical angle $J_{twist}$ was validated by comparing the distributions of simulated and experimentally measured FRET efficiencies in a stacked-X four-way junction. FRET efficiencies between Cy3 (donor) and Cy5 (acceptor) dyes covalently conjugated to a flexible four-way junction in two isomers denoted by iso-I (dyes on arms 2 and 3) and iso-II (dyes on arms 1 and 2). All DNA strands were purchased from Integrated DNA Technologies Inc. at a 25 or 100 nanomol (nmole, 1 nmole=10$^9$ moles) synthesis scale. All of the strands were further purified using denaturing PAGE gel. The sequences of DNA oligos used to form all the structures were designed using the program Tiamat. A one-step annealing reaction was used to form each structure. The strands for four four-way junctions in each design are mixed with final concentration as 0.2 mM in 1×TAE-Mg$^{2+}$ buffer (20 mM Tris, pH 7.6, 2 mM EDTA, 12.5 mM MgCl$_2$). The oligonucleotide mixture was annealed in a thermocycler that was programmed to cool from 95° C. to 4° C. in total 12 hours: 94° C. to 86° C. at 4° C. per 5 minutes; 85° C. to 70° C. at 1° C. per 5 minutes; 70° C. to 40° C. at 1° C. per 15 minutes; 40° C. to 25° C. at 1° C. per 10 minutes; then held at 4° C.

The standard value of rotational junction stiffness $k_{r3}$=135.3 pN nm/rad corresponding to the inter-helical angle $J_{twist}$ is multiplied by the factor a=0.2, 2, 20, 200, and 2000 in independent replicates. The simulated probability densities and their means were determined and compared to the experimentally measured probability densities of FRET. First, the atomistic structures of the two isomers, iso-I and iso-II, were generated of a stacked-X four-way junction where each arm consists of 11 bps. For each isomer, a trajectory of 1,000 conformations was generated using finite element normal mode analysis. The two accessible volumes (AVs) of the Cy3 and Cy5 tethered dyes were generated in each conformation. The mean FRET efficiency in a given conformation was then calculated using static averaging given by Equation 7.

$$E = \left\langle 1 \bigg/ \left[ 1 + \frac{2}{3\kappa^2}\left(\frac{R}{R_0}\right)^6 \right] \right\rangle \quad (7)$$

where R is the distance between two points $x_{Cy3}$ and $x_{Cy5}$ randomly chosen from the AVs of Cy3 and Cy5, respectively, in the current conformation. The Förster radius between Cy3 and Cy5 is $R_0$=5.4 nm when the orientation factor $\kappa^2$=⅔. The actual orientation factor considering rotation of the dyes was calculated with equation 8.

$$\kappa = e_1 \cdot e_2 - 3(e_1 \cdot e_{12})(e_{12} \cdot e_2) \quad (8)$$

where $e_1$ and $e_2$ are two random unit vectors, and $e_{12}$=($x_{Cy5}$−$x_{Cy3}$)/R. Thus, 1,000 mean FRET efficiencies were obtained from the trajectory of each isomer. The probability density of the mean FRET efficiencies was compared to experiment. The distributions of simulated FRET efficiencies with a=1, 2, 20, 200, and 2000 are all insensitive to the value of a and all agree with the experiment. In contrast, the simulated FRET efficiencies with a=0.2 follow a flat and broad distribution, differing significantly from experiment. These results suggest a lower bound of 0.2 $k_3$ on the rotational stiffness coefficient, justifying the value found from fluctuation analysis in the preceding MD simulations.

2.6 Example 3D Structures

Here, the ability of a coarse-grained mechanical model of the immobile four-way junction to predict the large-scale solution structure of diverse DNA architectures is tested. The model is tested by applying it to curved 2D and 3D ring-like objects, a sheet-like ribbon that adopts right-versus left-handed twist depending on underlying sequence topology, a 3D crystal structure of a tensegrity motif, and several variants of a gridiron-like structure in which four-way junctions undergo large-scale scissor-like rotations. Structural predictions are in quantitative agreement with experimental data, providing evidence that the model offers a general framework for the prediction of 3D solution structure of complex, high molecular weight nucleic acid architectures that have an increasing number of applications in fundamental and applied biomolecular science and technology.

The designs considered here include ring-like, chiral, and lattice-like structures. Non-intuitive structural predictions are tested experimentally, providing evidence that the model proposed will prove broadly useful for quantitative prediction of the solution structure of complex self-assembled nucleic acids that cannot be accessed easily experimentally or by any existing computational approach.

FIG. 11A is a block diagram that illustrates example dependence of 3D structure on values of certain parameters, according to an embodiment. The simple tile design is made up of four four-way stacked junctions separated by $n_x$ base pairs in one direction and $n_y$ base pairs in an orthogonal direction. FIG. 11 shows the final 3D solutions for $n_x$, and $n_y$ varying independently from 20 to 22 base pairs. The chirality, which can be flat (F), left-handed (LH), or right-handed (RH), is defined with respect to the x-direction and indicated for each row and column. FIG. 11B is a block diagram that illustrates example truth table for the 3D structure of FIG. 11A, according to an embodiment. The 3×3 truth table combines the effects of deletion or insertion in x-direction (first item in each entry) and y-direction (second item). Entries with conflicting handedness are marked in bold font.

The [$n_x$, $n_y$]=[21, 21] bps tile structures were previously studied by Mao et al. (Mao C D, Sun W Q, Seeman N C, "Designed two-dimensional DNA Holliday junction arrays visualized by atomic force microscopy," *J Am Chem Soc* v121(23), pp5437-5443, 1999.). In their original design, this lattice spacing between four-way junctions was chosen in order to generate a flat ribbon structure from which the inter-helical angle of 60° could be resolved clearly using AFM. Here, the tiles were modeled and experimentally tested with systematic variations on this design in which the x- and y-duplexes were changed to consist of either 20, 21, or 22 base pairs (bps), from which either intuitive or non-intuitive right- and left-handed twist emerged, as shown in FIG. 11A. Whereas the basic building block of 2D lattices is the parallelogram comprising four four-way junctions connected by four duplexes, the natural 10.5 bp/turn geometry of B-form DNA indicates that these parallelograms should twist overall if duplex arms deviate from their canonical helical repeat of 21, 42, 63, etc. bp/turn.

Simple geometric arguments result in the twisting of the parallelogram about the x-direction in six cases with a single deletion or insertion in either the x- or y-direction as shown in FIG. 11A and truth table in FIG. 11B. For example, a single deletion/insertion in the x-direction ($n_x$=20 or 22 bps) results in a left-/right-handed twist about the x-direction. In contrast, a single deletion/insertion in the y-direction ($n_y$=20 or 22 bps) results in a right-/left-handed twist about the x-direction. While seven cases in the table of FIG. 11A consist of entries of chirality that do not conflict with the truth table of FIG. 11B, from which the overall ribbon chirality may be predicted geometrically, there are two cases $[n_x, n_y]$=[20, 20] and [22, 22] bps for which the chirality induced by insertions/deletions contradicts one another, requiring a physics-based model to predict the resulting overall ribbon structure. Cases in which the ribbon is predicted to be flat by one arm and right-/left-handed by the other provide additional evidence for the model to predict shape quantitatively. Interestingly, the [20, 20] design is predicted to be left-handed about the x-direction, whereas the [22, 22] design is predicted to be right-handed. Chirality in the other seven cases agrees with the simple geometric predictions of the truth table. N×4 lattices were studied experimentally instead of N×2 in order to be resolvable using AFM and TEM, which agree with predictions of the model for the cases in which folding and self-assembly was successful.

Figure 12A:
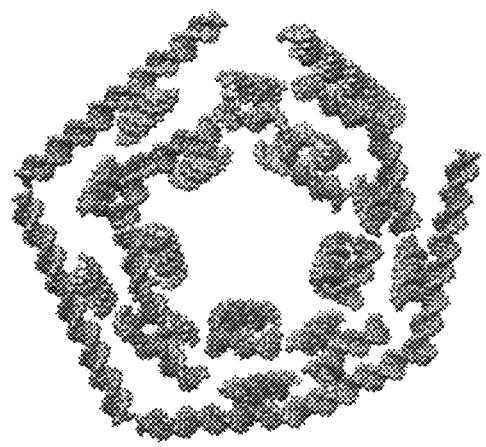
FIG. 12A through FIG. 12C are block diagrams that illustrate perpendicular views of initial positions of bases in a DNA nanostructure, according to an embodiment.
Figure 12B:
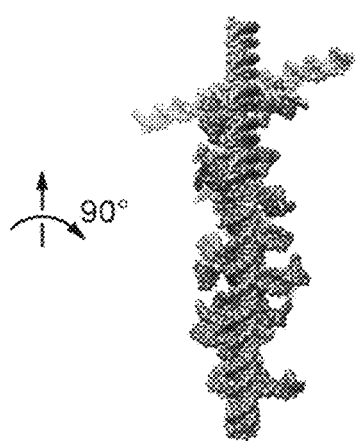
Figure 12C:
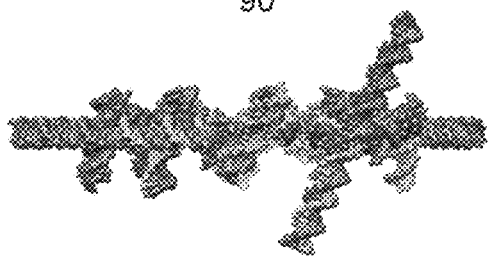
Figure 12D:
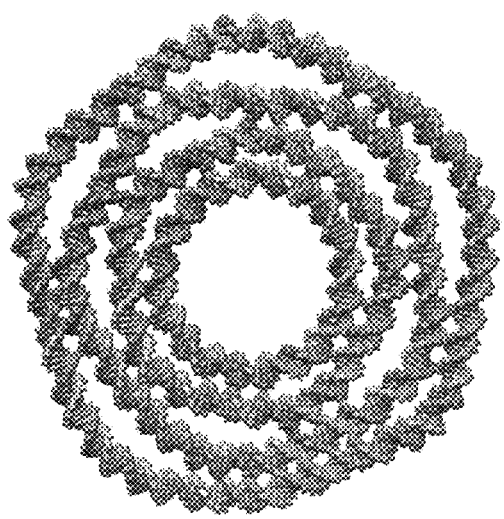
FIG. 12D is a block diagram that illustrates a final solution for a 3D structure of bases in the DNA nanostructure, according to an embodiment.

To test the ability of this procedure to compute the equilibrium shape of highly bent or curved 2D objects, it was applied to a concentric ring structure consisting of four rings designed to reside in a 2D plane with circumferences of 100, 150, 200, and 250 bps, respectively, with inner diameter of 11 nm and outer diameter of 26 nm, as illustrated in FIG. 3. FIG. 12A through FIG. 12C are block diagrams that illustrate perpendicular views of initial positions of bases in a DNA nanostructure, according to an embodiment. The initial shapes of the finite element models of DNA nanostructures in FIG. 12A through FIG. 12C were generated from the Tiamat design files and fed into the finite element solver to compute the final solution shape, and show many wide gaps (misalignments). FIG. 12D is a block diagram that illustrates a final solution for a 3D structure of bases in the DNA nanostructure, according to an embodiment, using the method of FIG. 9.

While the equilibrium solution shape remained planar, as intended, individual helices adopted straightened configurations intervening neighboring four-way junctions in order to minimize their overall mechanical free energy.

In contrast, application of the model to a scaffolded DNA origami structure consisting of 9 concentric rings previously designed and analyzed experimentally using AFM exhibited significant out-of-plane distortion in addition to in-plane duplex bulging despite the absence of any electrostatic repulsion between neighboring helices.

To test the ability of the model to predict the 3D solution shape of a curved architecture, it was applied to a 12-layer DNA origami hemisphere with outer diameter 44 nm. While the overall solution structure is predicted to be hemispherical, as designed, the upper quadrant collapsed slightly due to the mismatch of intervening DNA duplexes in that region, likely because the model assumes 1.85 nm inter-helical distance at four-way junctions, whereas 2.5 nm was assumed in the earlier work. Specifically, in the 2D designs shown in FIG. 12, and others, not shown, and 3D designs, not shown, the structures were designed so that differences in their ring radii, denoted by Δr, of two consecutive layers equal about 2.5 nm by assuming 0.34 nm axial length of each bp. For example, the outermost two layers in the 4-layer ring of FIG. 3 and FIG. 12D consist of 200 and 250 bps and Δr≈2.5 nm. This geometric confinement likely leads to the five bulges between two neighboring immobile four-way junctions in the outermost two layers with increased inter-helical distance and increased curvature in the outermost layer.

Four-way junctions have also been used to assemble 3D extended crystals consisting of a tensegrity motif. The ability of the method 900 to be applied to such crystals by predicting the equilibrium shape of this previously designed 3D crystal was tested by simulating a rhombohedral crystal with the unit cell as a DNA tensegrity triangle. The predicted crystal structure was compared with experimental PDB entry by computing the root-mean-square deviation (RMSD) between the central model unit cell and the X-ray crystallographic structure (PDB ID: 3GBI), indicating a maximum deviation at the four-way junctions of up to 5.3 Angstrom (Å, 1 Å=$10^{-10}$ meters) that is measured on an overall resolution of 4 Å of the published structure. Altering the ground-state angle and mechanical properties assumed for the four-way junction did not significantly affect this difference, suggesting that this tensegrity motif is highly stable mechanically due to the topological constraints imposed by the repeating unit cell, which consists of short duplexes with 7 and 14 bps.

The method was also applied to predict the solution structure of a highly strained four-way junction scaffolded origami gridiron structure consisting of a long, continuous scaffold strand that traverses the entire structure in periodically repeating unit cells in which neighboring four-way junctions are twisted by 150° and 30° to target neighboring 90° angles on a lattice, deviating greatly from their 60° equilibrium angle. Three gridiron structures were simulated in which the two neighboring junctions are connected by duplexes consisting of 21, 42, and 63 bps each. The three designs comprise 119, 81, and 49 four-way junctions, resulting in 3.27, 4.44, and 4.36 MDa molecular weights of 5.0, 6.8, and 6.7 kbps total, respectively.

Prediction of the solution structure using the default four-way junction scissor-like stiffness of 135.3 pN nm/rad of $J_{twist}$ resulted in highly distorted structures that were inconsistent with experimental observations. Instead, in order to generate solution structures in agreement with experiment, the four-way junction stiffness of $J_{twist}$ had to be reduced by an order of magnitude, which is not necessarily unexpected given the very large rotations that the four-way junction must undergo to realize this folded shape. Importantly, while this empirical modeling result subsequently agreed well with experimental data, it is unclear whether the immobile four-way junction truly exhibits such nonlinear softening with increasing inter-helical angle, or whether it may adopt distinct local free energy minimum conformational states. Single-molecule experimental studies together with force-biasing all-atom simulations may be useful to examine this result in more detail.

All three gridiron structures have rhomboidal shapes in which the acute angles θ=60°-70°. In comparison, the measured overall angle is 76°±7° in the synthesized gridiron where neighboring junctions are connected by 21-bp duplex. AFM images of all three gridirons indicate that the angle θ in the gridirons is affected significantly by thermal fluctuations or heterogeneity in self-assembled constructs. Equilibrium solution shape angles of the gridirons are predicted from the finite element model to be θ=59°±4°, 70°±4°, and 60°±7°, respectively, in reasonable agreement with experiment. Normal mode analysis provides equilibrium angle distributions due to thermal fluctuations and structural flexibility for the same angle, θ, based on the ground-state equilibrium finite element solution shapes.

Sensitivity analysis of the rotational junction stiffness $k_{r3}$ corresponding to the inter-helical angle $J_{twist}$ and the bend and twist moduli of DNA nicks are presented here. The standard values of $k_{r3}$ were 135.3 pN nm/rad used to generate solution shapes of standard B-form structures and 13.53 pN nm/rad for duplexes with nicks. The standard values of the bend and twist moduli of DNA nicks used to generate solution shapes are identical to those of DNA duplexes. Solution shapes calculated using $k_{r3}$ equal to the standard value multiplied by a factor a and the bend and twist moduli of nicked DNA equal to the standard values multiplied by a factor b. The solution shapes of the 2D and 3D structures containing concentric rings and the 3D crystal structure of a tensegrity motif are insensitive to the rotational junction stiffness $k_{r3}$ and the bend and twist moduli of nicks.

For the gridiron shapes of FIG. 11A, the [21, 21] lattices have zero mechanical free energy, thus the solution shapes are independent of the stiffness parameters. In contrast, the [22, 21], [20, 21], [22, 22], and [20, 20] lattices exhibit relatively high internal stresses and show structural sensitivity to the stiffness parameters. The chirality of the [22, 22] lattices is also sensitive to the bend and twist moduli of nicks. The standard value of rotational junction stiffness $k_{r3}$=135.3 pN nm/rad corresponding to the inter-helical angle $J_{twist}$ is multiplied by the factor a=0.1 and 10. The standard values of the bend and twist moduli of DNA nicks are multiplied by the factor b=0.1, 0.01, and 0.001. The solutions for the 40×2 and 40×4 gridiron lattices are determined. As the bend and twist moduli of DNA nicks decrease, the chirality of the 40×2 and 40×4 lattices gradually changes from right-handed (RH) to left-handed (LH).

In addition, structures with highly strained four-way junctions show highly distorted solution shapes with increased rotational junction stiffness $k_{r3}$ or decreased bend and twist moduli of DNA nicks.

3. Computational Hardware Overview

Figure 13:
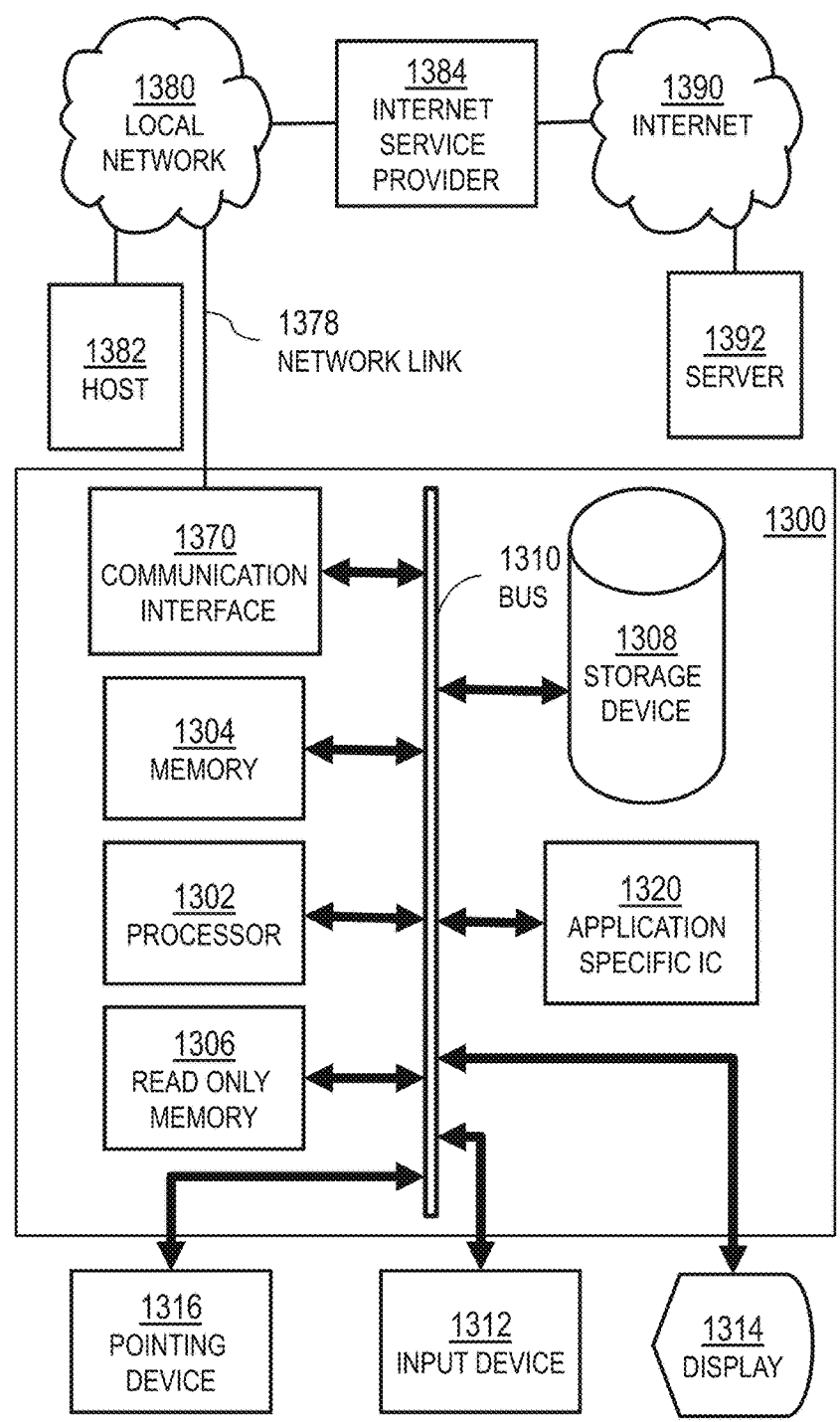
FIG. 13 is a block diagram that illustrates a computer system upon which an embodiment of the invention may be implemented.

FIG. 13 is a block diagram that illustrates a computer system 1300 upon which an embodiment of the invention may be implemented. Computer system 1300 includes a communication mechanism such as a bus 1310 for passing information between other internal and external components of the computer system 1300. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1300, or a portion thereof, constitutes a means for performing one or more steps of one or more methods described herein.

A sequence of binary digits constitutes digital data that is used to represent a number or code for a character. A bus 1310 includes many parallel conductors of information so that information is transferred quickly among devices coupled to the bus 1310. One or more processors 1302 for processing information are coupled with the bus 1310. A processor 1302 performs a set of operations on information. The set of operations include bringing information in from the bus 1310 and placing information on the bus 1310. The set of operations also typically include comparing two or more units of information, shifting positions of units of information, and combining two or more units of information, such as by addition or multiplication. A sequence of operations to be executed by the processor 1302 constitutes computer instructions.

Computer system 1300 also includes a memory 1304 coupled to bus 1310. The memory 1304, such as a random access memory (RAM) or other dynamic storage device, stores information including computer instructions. Dynamic memory allows information stored therein to be changed by the computer system 1300. RAM allows a unit of information stored at a location called a memory address to be stored and retrieved independently of information at neighboring addresses. The memory 1304 is also used by the processor 1302 to store temporary values during execution of computer instructions. The computer system 1300 also includes a read only memory (ROM) 1306 or other static storage device coupled to the bus 1310 for storing static information, including instructions, that is not changed by the computer system 1300. Also coupled to bus 1310 is a non-volatile (persistent) storage device 1308, such as a magnetic disk or optical disk, for storing information, including instructions, that persists even when the computer system 1300 is turned off or otherwise loses power.

Information, including instructions, is provided to the bus 1310 for use by the processor from an external input device 1312, such as a keyboard containing alphanumeric keys operated by a human user, or a sensor. A sensor detects conditions in its vicinity and transforms those detections into signals compatible with the signals used to represent information in computer system 1300. Other external devices coupled to bus 1310, used primarily for interacting with humans, include a display device 1314, such as a cathode ray tube (CRT) or a liquid crystal display (LCD), for presenting images, and a pointing device 1316, such as a mouse or a trackball or cursor direction keys, for controlling a position of a small cursor image presented on the display 1314 and issuing commands associated with graphical elements presented on the display 1314.

In the illustrated embodiment, special purpose hardware, such as an application specific integrated circuit (IC) 1320, is coupled to bus 1310. The special purpose hardware is configured to perform operations not performed by processor 1302 quickly enough for special purposes. Examples of application specific ICs include graphics accelerator cards for generating images for display 1314, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1300 also includes one or more instances of a communications interface 1370 coupled to bus 1310. Communication interface 1370 provides a two-way communication coupling to a variety of external devices that operate with their own processors, such as printers, scanners and external disks. In general the coupling is with a network link 1378 that is connected to a local network 1380 to which a variety of external devices with their own processors are connected. For example, communication interface 1370 may be a parallel port or a serial port or a universal serial bus (USB) port on a personal computer. In some embodiments, communications interface 1370 is an integrated services digital network (ISDN) card or a digital subscriber line (DSL) card or a telephone modem that provides an information communication connection to a corresponding type of telephone line. In some embodiments, a communication interface 1370 is a cable modem that converts signals on bus 1310 into signals for a communication connection over a coaxial cable or into optical signals for a communication connection over a fiber optic cable. As another example, communications interface 1370 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1370 sends and receives electrical, acoustic or electromagnetic signals, including infrared and optical signals, that carry information streams, such as digital data.

The term computer-readable medium is used herein to refer to any medium that participates in providing information to processor 1302, including instructions for execution. Such a medium may take many forms, including, but not limited to, non-volatile media, volatile media and transmission media. Non-volatile media include, for example, optical or magnetic disks, such as storage device 1308. Volatile media include, for example, dynamic memory 1304. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1302, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1302, except for carrier waves and other signals.

Logic encoded in one or more tangible media includes one or both of processor instructions on a computer-readable storage media and special purpose hardware, such as ASIC 1320.

Network link 1378 typically provides information communication through one or more networks to other devices that use or process the information. For example, network link 1378 may provide a connection through local network 1380 to a host computer 1382 or to equipment 1384 operated by an Internet Service Provider (ISP). ISP equipment 1384 in turn provides data communication services through the public, world-wide packet-switching communication network of networks now commonly referred to as the Internet 1390. A computer called a server 1392 connected to the Internet provides a service in response to information received over the Internet. For example, server 1392 provides information representing video data for presentation at display 1314.

The invention is related to the use of computer system 1300 for implementing the techniques described herein. According to one embodiment of the invention, those techniques are performed by computer system 1300 in response to processor 1302 executing one or more sequences of one or more instructions contained in memory 1304. Such instructions, also called software and program code, may be read into memory 1304 from another computer-readable medium such as storage device 1308. Execution of the sequences of instructions contained in memory 1304 causes processor 1302 to perform the method steps described herein. In alternative embodiments, hardware, such as application specific integrated circuit 1320, may be used in place of or in combination with software to implement the invention. Thus, embodiments of the invention are not limited to any specific combination of hardware and software.

The signals transmitted over network link 1378 and other networks through communications interface 1370, carry information to and from computer system 1300. Computer system 1300 can send and receive information, including program code, through the networks 1380, 1390 among others, through network link 1378 and communications interface 1370. In an example using the Internet 1390, a server 1392 transmits program code for a particular application, requested by a message sent from computer 1300, through Internet 1390, ISP equipment 1384, local network 1380 and communications interface 1370. The received code may be executed by processor 1302 as it is received, or may be stored in storage device 1308 or other non-volatile storage for later execution, or both. In this manner, computer system 1300 may obtain application program code in the form of a signal on a carrier wave.

Various forms of computer readable media may be involved in carrying one or more sequence of instructions or data or both to processor 1302 for execution. For example, instructions and data may initially be carried on a magnetic disk of a remote computer such as host 1382. The remote computer loads the instructions and data into its dynamic memory and sends the instructions and data over a telephone line using a modem. A modem local to the computer system 1300 receives the instructions and data on a telephone line and uses an infra-red transmitter to convert the instructions and data to a signal on an infra-red a carrier wave serving as the network link 1378. An infrared detector serving as communications interface 1370 receives the instructions and data carried in the infrared signal and places information representing the instructions and data onto bus 1310. Bus 1310 carries the information to memory 1304 from which processor 1302 retrieves and executes the instructions using some of the data sent with the instructions. The instructions and data received in memory 1304 may optionally be stored on storage device 1308, either before or after execution by the processor 1302.

Figure 14:
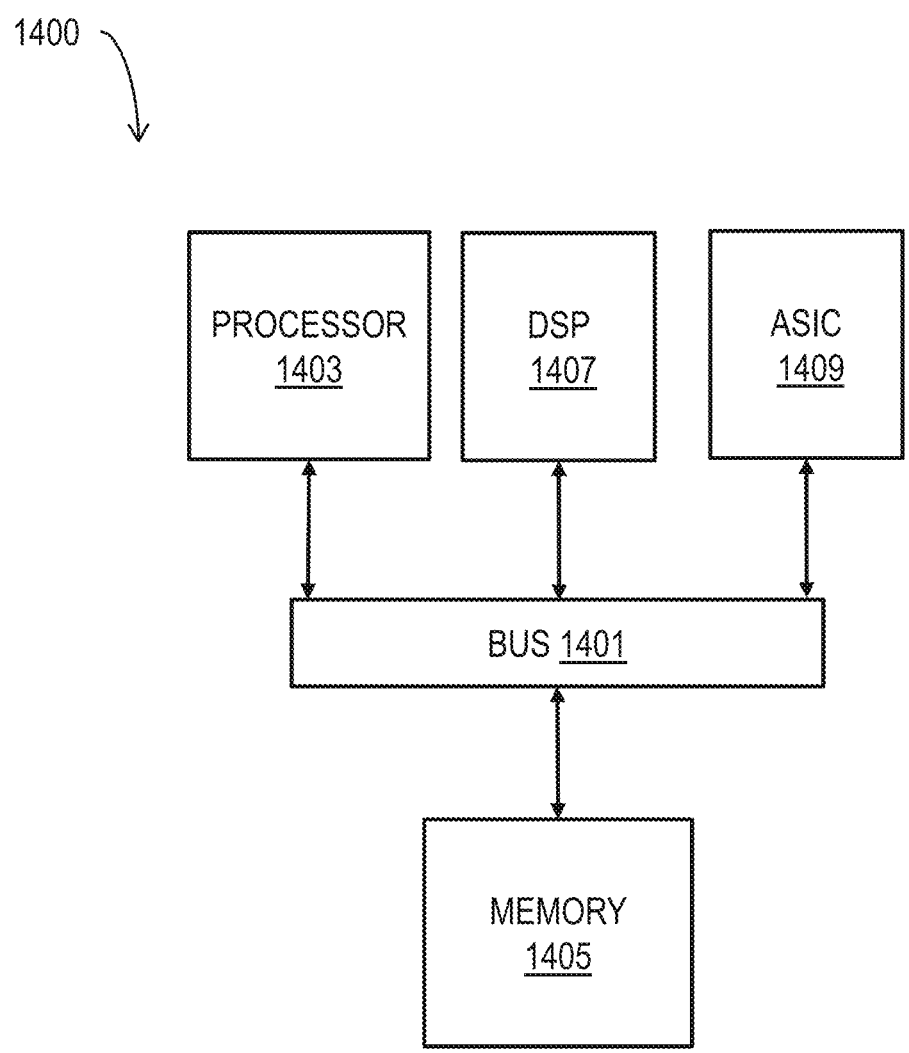
FIG. 14 illustrates a chip set upon which an embodiment of the invention may be implemented.

FIG. 14 illustrates a chip set 1400 upon which an embodiment of the invention may be implemented. Chip set 1400 is programmed to perform one or more steps of a method described herein and includes, for instance, the processor and memory components described with respect to FIG. 13 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1400, or a portion thereof, constitutes a means for performing one or more steps of a method described herein.

In one embodiment, the chip set 1400 includes a communication mechanism such as a bus 1401 for passing information among the components of the chip set 1400. A processor 1403 has connectivity to the bus 1401 to execute instructions and process information stored in, for example, a memory 1405. The processor 1403 may include one or more processing cores with each core configured to perform independently. A multi-core processor enables multiprocessing within a single physical package. Examples of a multi-core processor include two, four, eight, or greater numbers of processing cores. Alternatively or in addition, the processor 1403 may include one or more microprocessors configured in tandem via the bus 1401 to enable independent execution of instructions, pipelining, and multithreading. The processor 1403 may also be accompanied with one or more specialized components to perform certain processing functions and tasks such as one or more digital signal processors (DSP) 1407, or one or more application-specific integrated circuits (ASIC) 1409. A DSP 1407 typically is configured to process real-world signals (e.g., sound) in real time independently of the processor 1403. Similarly, an ASIC 1409 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1403 and accompanying components have connectivity to the memory 1405 via the bus 1401. The memory 1405 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1405 also stores the data associated with or generated by the execution of one or more steps of the methods described herein.

4. Extensions, Modifications and Alternatives

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items. elements or steps. Furthermore, the indefinite article "a" or "an" is meant to indicate one or more of the item, element or step modified by the article.

What is claimed is:

1. A method comprising:
   a. determining, for each junction type of one or more nucleic acid junction types, a plurality of values corresponding to a plurality of fixed parameters that indicate a ground-state geometry and translational and rotational junction stiffness coefficients for perturbations from the ground-state geometry;
   b. obtaining design data that indicates, for a nucleic acid structure, a number of nucleic acid bases in each helix of a set of two or more helices, wherein the set of helices are joined at a corresponding junction, for a plurality of sets of helices in the nucleic acid structure, wherein the plurality of sets of helices are connected by a plurality of junctions;
   c. determining automatically on a processor initial positions of each base in the nucleic acid structure by connecting helices at junctions using the ground-state geometry of each junction, wherein the initial positions are in arbitrary three dimensional coordinates that are not confined to lattice coordinates;
   d. determining automatically on a processor a set of one or more misalignment vectors, wherein each misalignment vector indicates a difference in three dimensional coordinates and orientations between initial positions of a pair of bases that are not adjacent or coincident in the initial positions but are adjacent or coincident, respectively, in the design data;
   e. determining automatically on a processor one or more forces or moments or both at the plurality of junctions that reduce magnitudes corresponding to the set of misalignment vectors based on the set of misalignment vectors and the translational and rotational junction stiffness coefficients at each junction of the plurality of junctions;
   f. determining automatically on a processor a three dimensional structure comprising position and orientation in three dimensional coordinates of each base in the nucleic acid structure, by reducing the magnitudes corresponding to the set of misalignment vectors and balancing forces and moments across the nucleic acid structure using constraint equations; and
   g. performing steps b. through f. until the three dimensional structure is suitable for an intended purpose, then selecting and fabricating the nucleic acid structure based on the determined three dimensional structure.

2. A method as recited in claim 1, wherein the plurality of values corresponding to the plurality of fixed parameters that indicate the ground-state geometry and translational and rotational junction stiffness coefficients for perturbations from the ground-state geometry are constant values.

3. A method as recited in claim 1, wherein determining the one or more forces or moments or both at the plurality of junctions further comprises:
   representing the junctions and helices as elements in a finite element model implemented on a processor; and
   executing the finite element model on the processor to incrementally apply forces to incrementally reduce the magnitudes and to propagate the forces through the plurality of junctions.

4. A method as recited in claim 3, wherein the misalignment vectors are represented by alignment elements of the finite element model.

5. A method as recited in claim 1, wherein each helix is a double helix (also called a duplex) of a deoxyribonucleic acid (DNA).

6. A method as recited in claim 1, wherein each helix is a single strand helix of a ribonucleic acid (RNA).

7. A method as recited in claim 1, wherein:
the method further comprises determining, for each helix type of one or more nucleic acid helix types, a plurality of helix values corresponding to a plurality of fixed helix parameters that indicate a helix ground-state geometry per base and translational and rotational helix stiffness coefficients for perturbations per base from the helix ground-state geometry per base; and
determining initial positions of each base in the nucleic acid structure further comprises connecting helices at junctions using the helix ground-state geometry of each helix and a number of bases of each helix.

8. A method as recited in claim 7, wherein the plurality of helix values corresponding to a plurality of fixed helix parameters are constant values.

9. A method as recited in claim 7, wherein determining the forces to reduce the magnitudes corresponding to the set of misalignment vectors further comprises determining one or more forces or moments or both on each helix of the plurality of sets of helices based on the translational and rotational helix stiffness coefficients and a number of bases of each helix.

10. A method as recited in claim 7, wherein determining the forces at the plurality of junctions further comprises:
representing at least one portion of each helix as a beam element in a finite element model implemented on a processor and representing each base of the at least one portion as a beam node of the beam element; and
executing the finite element model on the processor to incrementally apply forces to incrementally reduce the magnitudes and to propagate the forces through the plurality of junctions and plurality of sets of helices.

11. A method as recited in claim 1, further comprising interpreting the design data as a directed graph to determine each junction in the design data and each helix connected to each junction and a number of bases of each helix.

12. A method as recited in claim 1, wherein each base in each helix is appended, along with any intervening bases, to one junction to which the helix is connected and all bases in the helix appended to the one junction comprises one arm of the junction.

13. A method as recited in claim 1, wherein each misalignment vector also indicates a difference in orientation of the pair of bases that are not adjacent in the initial positions but are adjacent in the design data.

14. A method as recited in claim 1, wherein performing steps b. through f. further comprises modifying the design data and repeating said steps b. through f.

15. A non-transitory computer-readable medium carrying one or more sequences of instructions, wherein execution of the one or more sequences of instructions by one or more processors causes the one or more processors to perform the steps of:
a. determining, for each junction type of one or more nucleic acid junction types, a plurality of values corresponding to a plurality of fixed parameters that indicate a ground-state geometry and translational and rotational junction stiffness coefficients for perturbations from the ground-state geometry;
b. obtaining design data that indicates, for a nucleic acid structure, a number of nucleic acid bases in each helix of a set of two or more helices, wherein the set of helices are joined at a corresponding junction, for a plurality of sets of helices in the nucleic acid structure, wherein the plurality of sets of helices are connected by a plurality of junctions;
c. determining initial positions of each base in the nucleic acid structure by connecting helices at junctions using the ground-state geometry of each junction, wherein the initial positions are in arbitrary three dimensional coordinates that are not confined to lattice coordinates;
d. determining a set of one or more misalignment vectors, wherein each misalignment vector indicates a difference in three dimensional coordinates between initial positions of a pair of bases that are not adjacent or coincident in the initial positions but are adjacent or coincident, respectively, in the design data;
e. determining one or more forces or moments or both at the plurality of junctions to reduce magnitudes corresponding to the set of misalignment vectors based on the set of misalignment vectors and the translational and rotational junction stiffness coefficients at each junction of the plurality of junctions;
f. determining a three dimensional structure comprising position and orientation in three dimensional coordinates of each base in the nucleic acid structure, by reducing the magnitudes corresponding to the set of misalignment vectors and balancing forces and moments across the nucleic acid structure using constraint equations; and
g. performing steps b. through f. until the three dimensional structure is suitable for a particular purpose, then causing the nucleic acid structure to be selected and fabricated based on the determined three dimensional structure.

16. A system comprising:
a nucleic acid fabrication system;
at least one processor; and
at least one memory including one or more sequences of instructions,
the at least one memory and the one or more sequences of instructions configured to, with the at least one processor, cause an apparatus to perform at least the following,
a. determine, for each junction type of one or more nucleic acid junction types, a plurality of values corresponding to a plurality of fixed parameters that indicate a ground-state geometry and translational and rotational junction stiffness coefficients for perturbations from the ground-state geometry;
b. obtain design data that indicates, for a nucleic acid structure, a number of nucleic acid bases in each helix of a set of two or more helices, wherein the set of helices are joined at a corresponding junction, for a plurality of sets of helices in the nucleic acid structure, wherein the plurality of sets of helices are connected by a plurality of junctions;
c. determine initial positions of each base in the nucleic acid structure by connecting helices at junctions using the ground-state geometry of each junction, wherein the initial positions are in arbitrary three dimensional coordinates that are not confined to lattice coordinates;
d. determine a set of one or more misalignment vectors, wherein each misalignment vector indicates a difference in three dimensional coordinates and orientations between initial positions of a pair of bases that are not adjacent or coincident in the initial positions but are adjacent or coincident, respectively, in the design data;
e. determine forces at the plurality of junctions to reduce magnitudes corresponding to the set of misalignment vectors based on the set of misalignment vectors and the translational and rotational junction stiffness coefficients at each junction of the plurality of junctions;

f. determine a three dimensional structure comprising position and orientation in three dimensional coordinates of each base in the nucleic acid structure, by reducing the magnitudes corresponding to the set of misalignment vectors and balancing forces and moments across the nucleic acid structure using constraint equations; and g. performing steps b. through f. until the three dimensional structure is suitable for a particular purpose, then causing the nucleic acid structure to be selected and fabricated on the nucleic acid fabrication system based on the determined three dimensional structure.

* * * * *